US012376876B2

(12) United States Patent
Bono et al.

(10) Patent No.: US 12,376,876 B2
(45) Date of Patent: Aug. 5, 2025

(54) ROTARY OSCILLATING AND RECIPROCATING SURGICAL TOOL

(71) Applicant: GLOBUS MEDICAL, INC., Audubon, PA (US)

(72) Inventors: Peter L. Bono, Bingham Farms, MI (US); James D. Lark, King of Prussia, PA (US); John S. Scales, Clinton Township, MI (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 18/630,536

(22) Filed: Apr. 9, 2024

(65) Prior Publication Data

US 2024/0252195 A1    Aug. 1, 2024

Related U.S. Application Data

(63) Continuation of application No. 17/837,678, filed on Jun. 10, 2022, now Pat. No. 11,974,768, which is a continuation of application No. 16/784,331, filed on Feb. 7, 2020, now Pat. No. 11,357,529, which is a continuation-in-part of application No. 16/168,011, filed on Oct. 23, 2018, now Pat. No. 11,000,306, and a continuation-in-part of application No. 15/814,891, filed on Nov. 16, 2017, now Pat. No. 10,835,263.

(60) Provisional application No. 62/803,039, filed on Feb. 8, 2019, provisional application No. 62/575,775, filed on Oct. 23, 2017, provisional application No. 62/423,624, filed on Nov. 17, 2016.

(51) Int. Cl.
  *A61B 17/32* (2006.01)
  *A61B 17/3207* (2006.01)

(52) U.S. Cl.
  CPC ............... *A61B 17/32002* (2013.01); *A61B 17/320758* (2013.01); *A61B 2017/320028* (2013.01); *A61B 2017/320032* (2013.01)

(58) Field of Classification Search
  CPC .. A61B 17/32002; A61B 2017/320028; A61B 2017/320032; A61B 17/162; A61B 17/1622; A61B 17/1624; A61B 17/1626; A61B 17/1628
  See application file for complete search history.

(56) References Cited

U.S. PATENT DOCUMENTS

| | | | | |
|---|---|---|---|---|
| 5,975,900 A * | 11/1999 | Garman | ................. | A61C 1/185 433/105 |
| 5,993,454 A * | 11/1999 | Longo | .................... | B23Q 5/048 606/85 |
| 8,696,511 B2 * | 4/2014 | Steele | ..................... | B25B 17/02 475/14 |
| 9,295,815 B2 * | 3/2016 | Stevens | ........... | A61M 25/09041 |
| 10,925,623 B2 * | 2/2021 | Schaeffer | ......... | A61B 17/22012 |
| 2011/0066155 A1 * | 3/2011 | Del Rio | ............ | A61B 17/1624 606/85 |
| 2013/0303330 A1 * | 11/2013 | Stevens | ........... | A61M 25/09041 475/349 |

* cited by examiner

*Primary Examiner* — Anu Ramana

(57) ABSTRACT

A surgical tool that has a pair of transmissions coupled to one another to effect driving of a cutting tool in both an oscillating manner and a reciprocating manner. The transmissions are driven by a motor coupled to one of the transmissions.

20 Claims, 22 Drawing Sheets

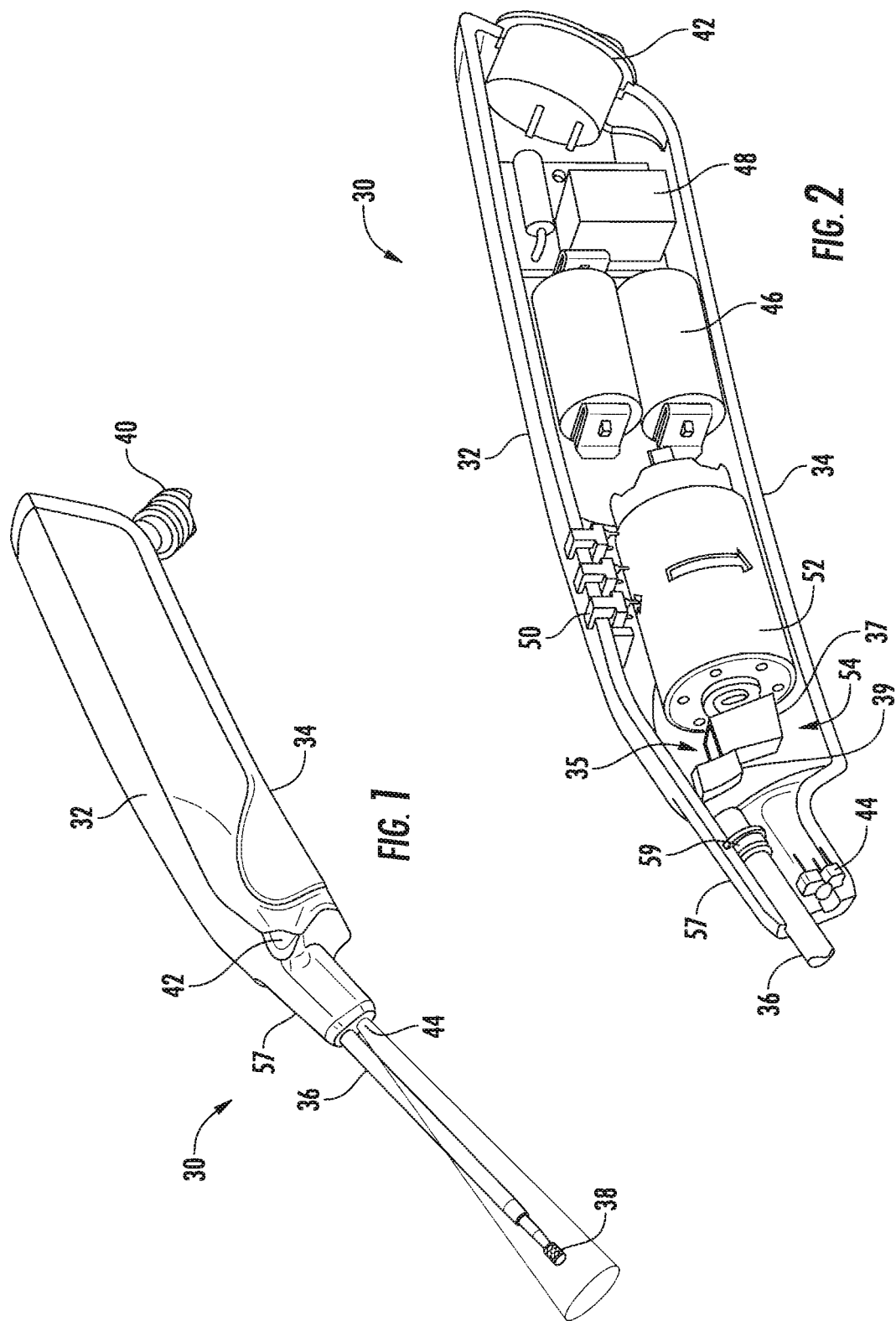

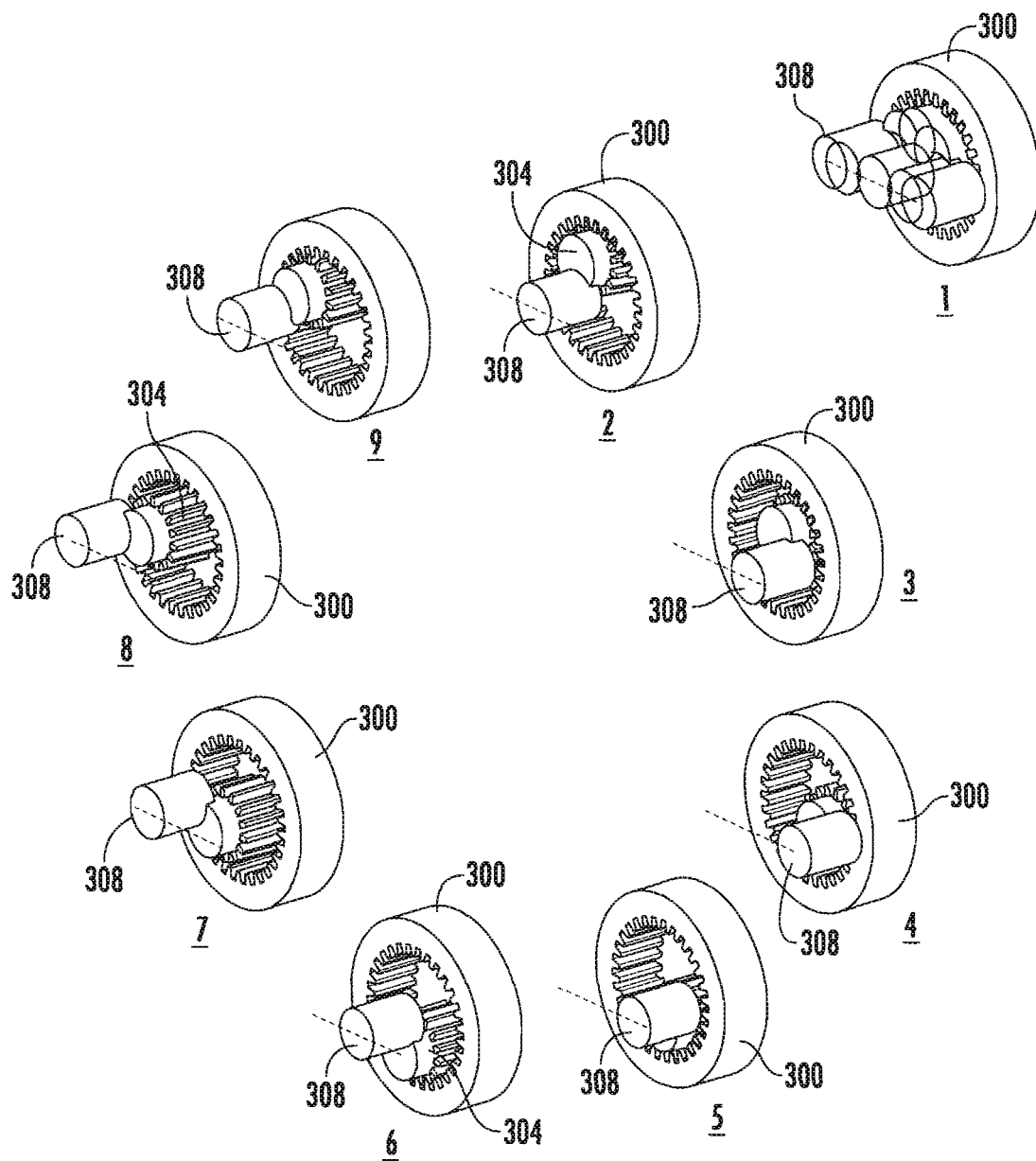
FIG. 7A1-7A9

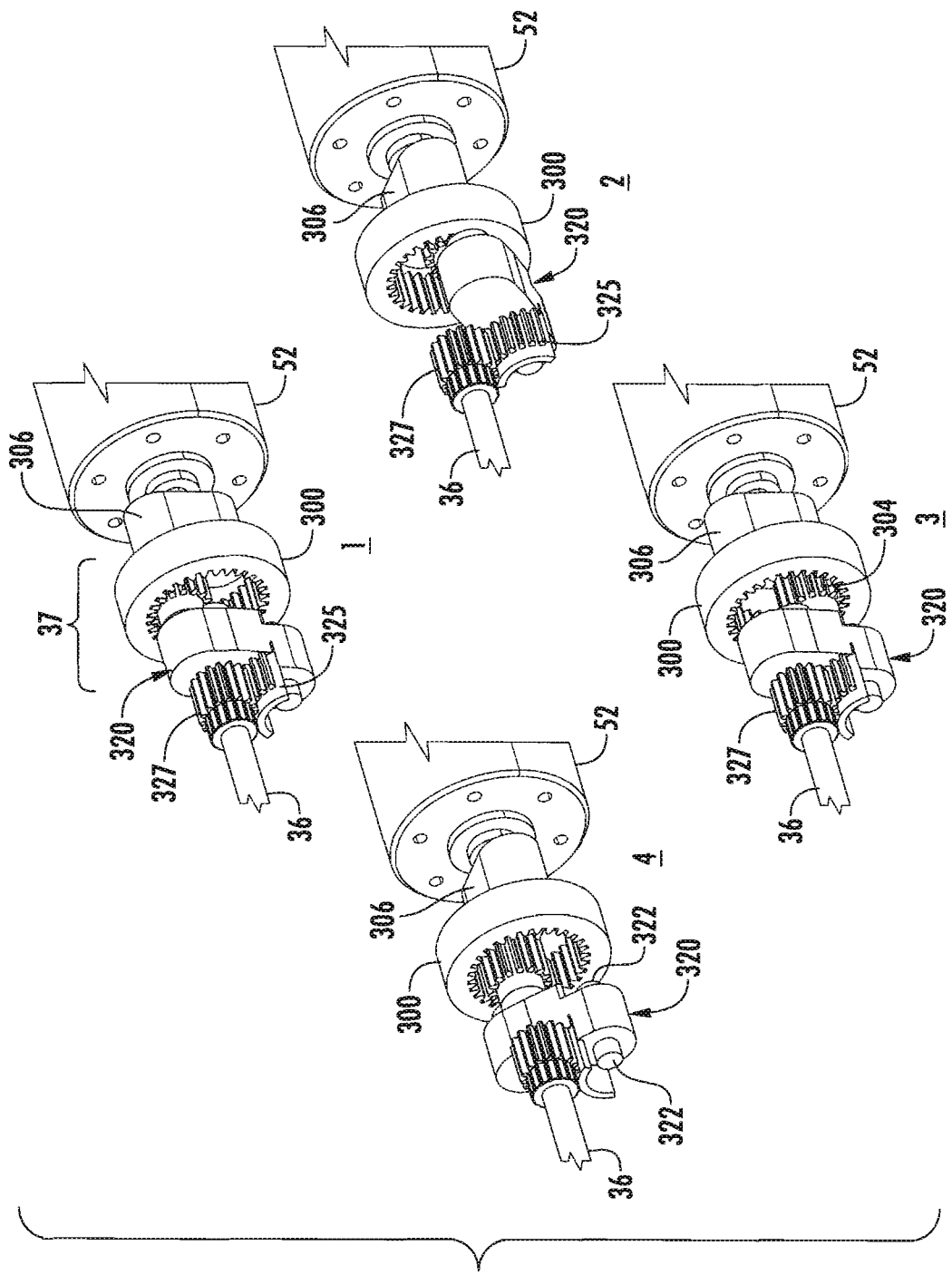
FIG. 7B1-7B4

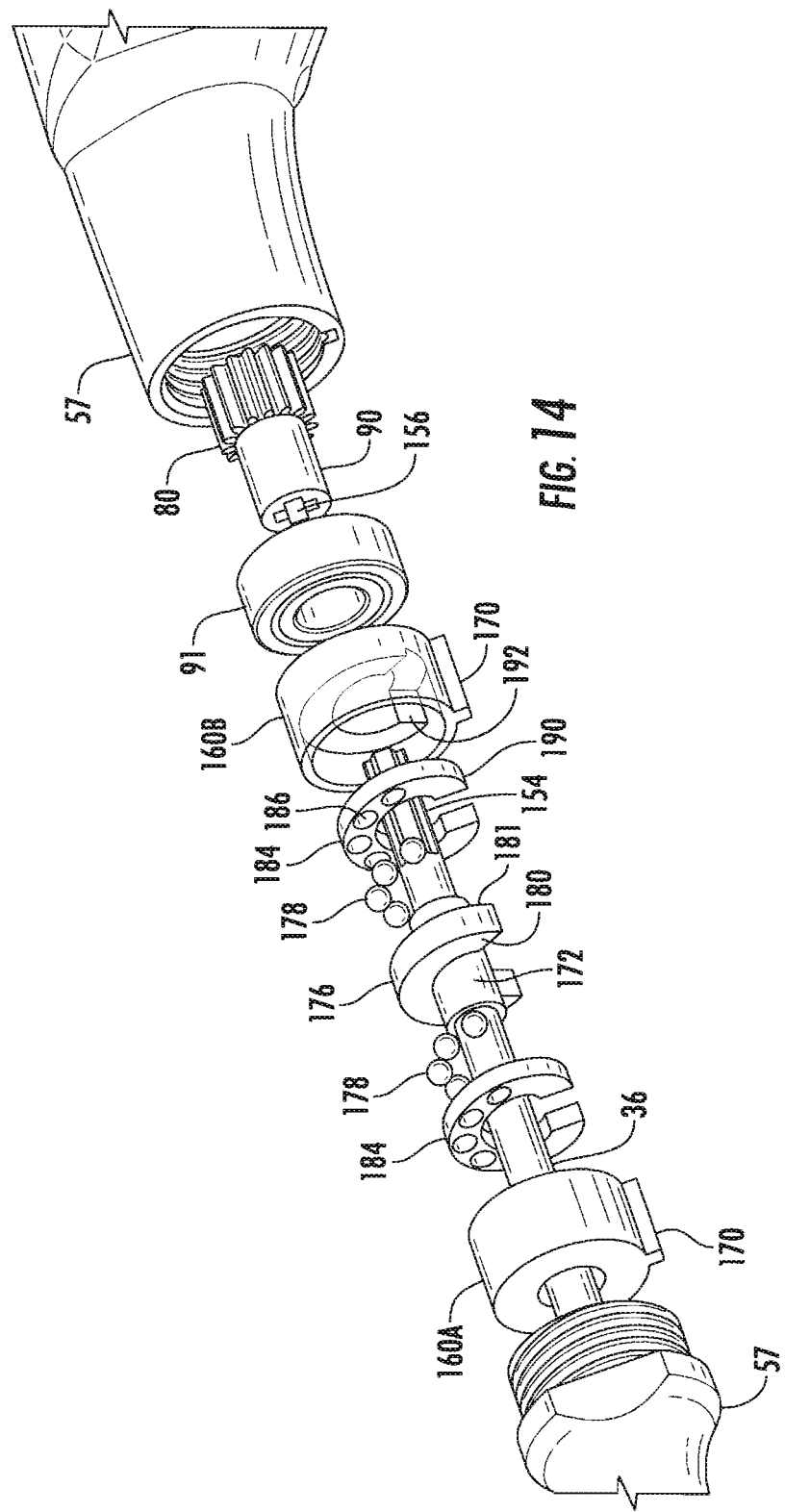

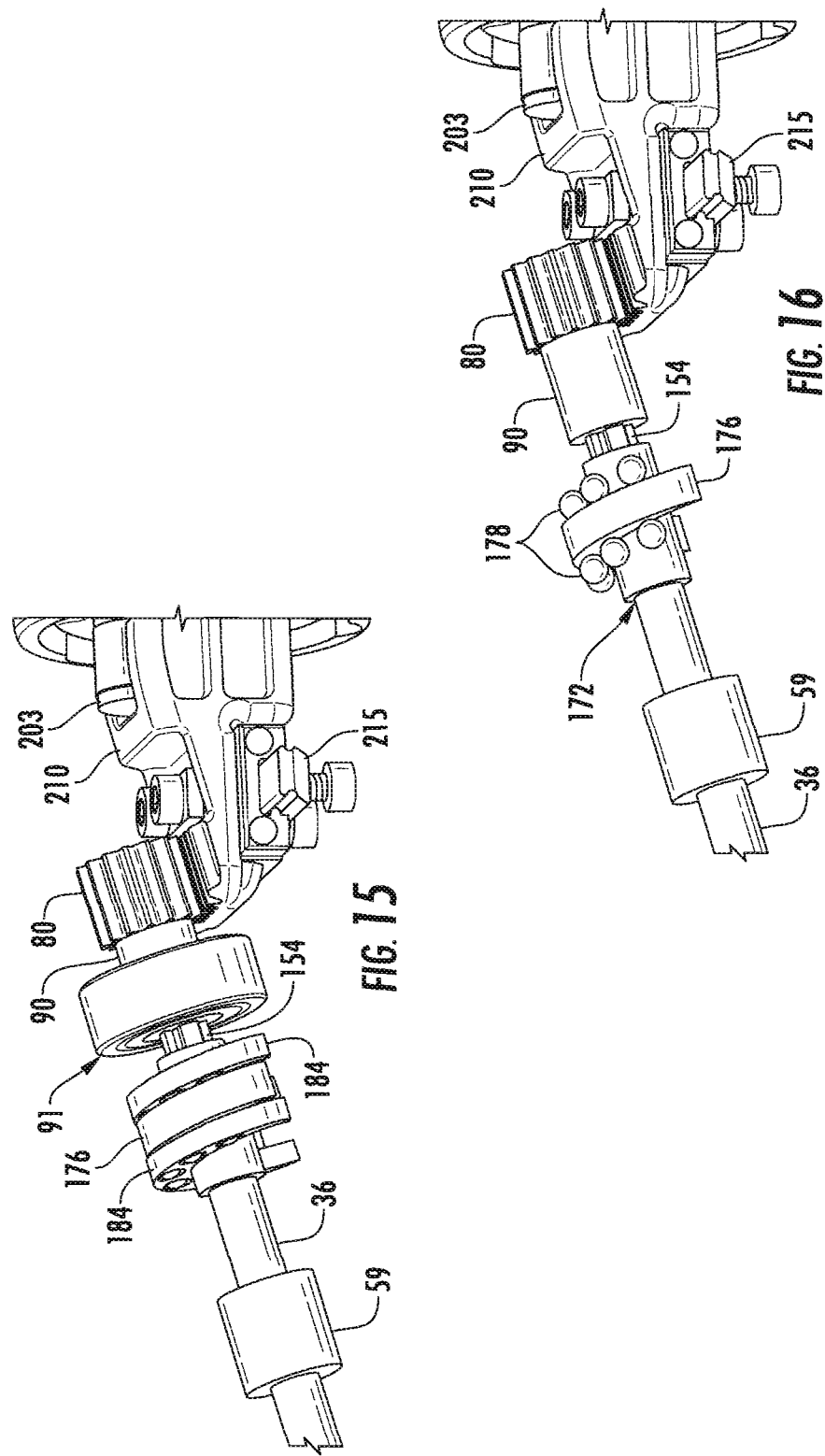

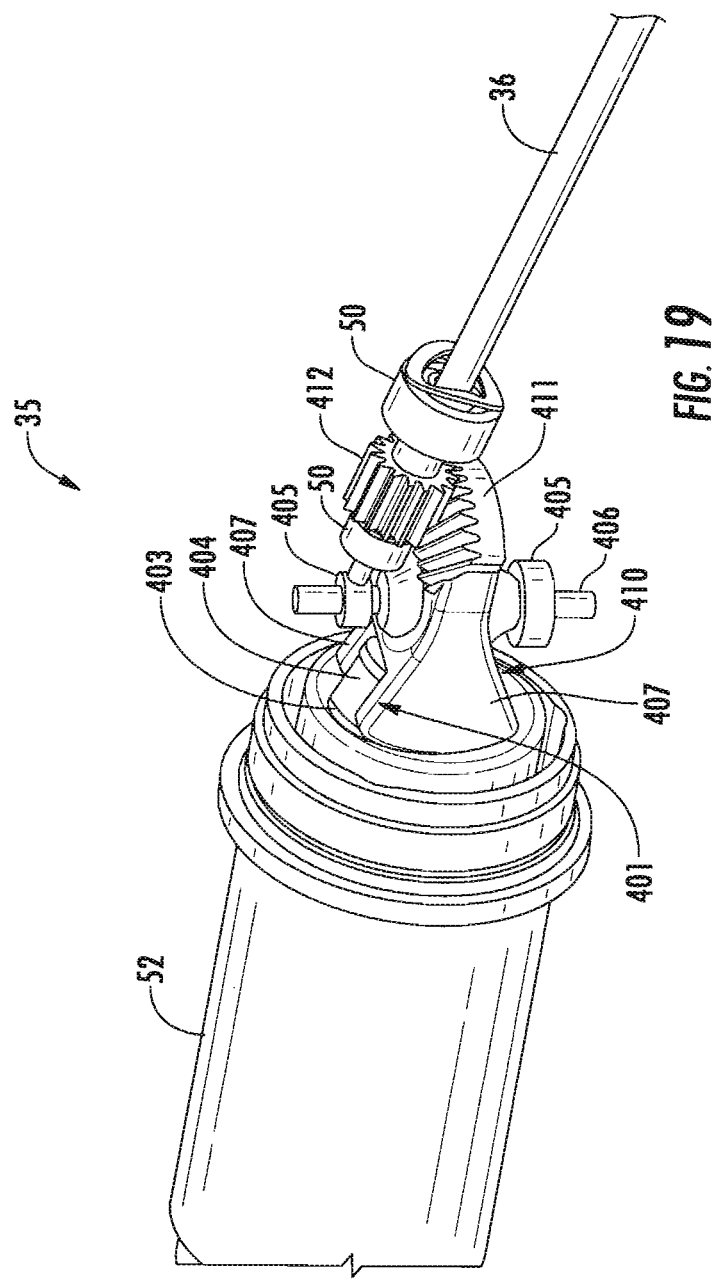

ROTARY OSCILLATING AND RECIPROCATING SURGICAL TOOL

PRIORITY CLAIM

The present application is a continuation of U.S. patent application Ser. No. 17/837,678 filed on Jun. 10, 2022, now U.S. Pat. No. 11,974,768, which is a continuation of U.S. patent application Ser. No. 16/784,331, filed Feb. 7, 2020, now U.S. Pat. No. 11,357,529, which (i) claims priority to U.S. Provisional Patent Application No. 62/803,039, filed Feb. 8, 2019, (ii) is a continuation-in-part of U.S. patent application Ser. No. 15/814,891, entitled "ROTARY OSCILLATING SURGICAL TOOL", filed Nov. 16, 2017, now U.S. Pat. No. 10,835,263, which claims priority to U.S. Provisional Patent Application No. 62/423,624, entitled "ROTARY OSCILLATING SURGICAL TOOL", filed Nov. 17, 2016, and (iii) is a continuation-in-part of U.S. patent application Ser. No. 16/168,011, entitled "ROTARY OSCILLATING/RECIPROCATING SURGICAL TOOL", filed Oct. 23, 2018, now U.S. Pat. No. 11,000,306, which claims priority to U.S. Provisional Patent Application No. 62/575,775, entitled "ROTARY OSCILLATING/RECIPROCATING SURGICAL TOOL", filed Oct. 23, 2017. The contents of the above referenced applications are incorporated herein by reference in their entirety.

FIELD OF THE INVENTION

The present invention relates to a powered surgical tool with a cutter adapted to modify tissue such as bone, cartilage and discs. The tool effects both rotary oscillation and longitudinal reciprocation of the cutter.

BACKGROUND OF THE INVENTION

The prior art has provided surgical tools having a rotary cutter adapted to modify tissue such as bone, cartilage and discs in a patient. Such tools, though, present a problem if the cutter encounters fibrous tissue such as muscle and nerves. Such fibrous tissue can wrap around the cutter and be damaged thereby. The prior art has also provided oscillating rotary tools for such surgical procedures, but the mechanisms used to effect oscillation of the cutter during its rotation do not operate smoothly due to the mechanisms used to effect oscillation. An advance in such oscillating tools is represented by our co-pending applications: U.S. Non-Provisional patent application Ser. No. 13/469,665, entitled "Rotary Oscillating Bone, Cartilage, and Disk Removal Tool Assembly, filed May 11, 2012; and now issued U.S. Pat. No. 10,194,922, issued on Feb. 5, 2019; U.S. International Application No. PCT/US2013/037071, entitled "Rotary Oscillating Bone, Cartilage, and Disk Removal Tool Assembly", filed Apr. 18, 2013; U.S. Non-Provisional patent application Ser. No. 13/647,101, entitled "Cutting Tool for Bone, Cartilage, and Disk Removal", filed Oct. 8, 2012, and now issued U.S. Pat. No. 9,232,953, issued on Jan. 12, 2016; U.S. International Application No. PCT/US2013/063182, entitled "Cutting Tool for Bone, Cartilage, and Disk Removal", filed Oct. 3, 2013; U.S. Provisional Patent Application No. 62/460,481, entitled "Surgical Rotary Tool", filed Feb. 17, 2017, U.S. Non-Provisional patent application Ser. No. 15/895,352, entitled "Surgical Rotary Tool", filed Feb. 13, 2018; and U.S. Non-Provisional patent application Ser. No. 15/932,361, entitled "Surgical Rotary Tool", filed Feb. 16, 2018; U.S. Provisional Patent Application No. 62/423,624, entitled "Rotary Oscillating Surgical Tool", filed Nov. 17, 2016, and U.S. Non-Provisional patent application Ser. No. 15/814,891, entitled "Rotary Oscillating Surgical Tool", filed Nov. 16, 2017; U.S. Provisional Patent Application No. 62/423,651, entitled "Robotic Surgical System", filed Nov. 17, 2016; U.S. Provisional Patent Application No. 62/423,677, entitled "Robotic Surgical System", filed Nov. 17, 2016, and U.S. Non-Provisional patent application Ser. No. 15/816,861, entitled "Robotic Surgical System", filed Nov. 17, 2017. The contents of each of the above referenced applications are herein incorporated by reference.

Such tools are typically small and lightweight, with little room for drive mechanisms. They tend to operate at high cutting speeds for cutting efficiency and control by a surgeon. Oscillations are on the order of at least about 10,000 oscillations per minute (5,000 orbits per minute), and may be 30,000-50,000 oscillations per minute or more. Reciprocation rate is preferably the same. An oscillation is movement of the cutter from one rotational position extreme to its other rotational extreme. Reciprocation is movement of the cutter from one linear movement position extreme to its other linear movement extreme. The cutter configuration and material being removed will determine cutter speed. Because of the high speed and need for precision placement and cutting, the tools need to be smooth in operation with little vibration.

SUMMARY OF THE INVENTION

According to one embodiment of the present invention, a surgical tool is provided with a housing, a cutter support shaft that is operably connected to a motor to effect oscillating rotation of the shaft, and a drive transmission configured between the motor and the shaft to effect oscillating rotary movement and simultaneous linear reciprocating movement of the shaft and cutter mounted to the shaft.

It is an objective of the instant invention to provide an oscillation/reciprocation effecting drive transmission that utilizes a first driver to effect rotary oscillation of a cutter and to simultaneously effect driving of a second driver that is operable to add longitudinal reciprocating movement to the cutter.

It is yet another objective of the instant invention to provide an oscillation/reciprocation effecting drive transmission that utilizes a rack and pinion gear arrangement to effect driving connection between the first and second drivers.

It is a still further objective of the instant invention to provide a reciprocation effecting driver coupled to the oscillation driver to effect simultaneous longitudinal reciprocation of the cutter shaft while it oscillates.

It is yet another objective of the instant invention to provide a drive transmission that is simple in construction.

Other objects and advantages of this invention will become apparent from the following description taken in conjunction with any accompanying drawings wherein are set forth, by way of illustration and example, certain embodiments of this invention. Any drawings contained herein constitute a part of this specification, include exemplary embodiments of the present invention, and illustrate various objects and features thereof.

BRIEF DESCRIPTION OF THE FIGURES

FIG. 1 is a perspective view of the surgical tissue removal tool;

FIG. 2 is a cutaway fragmentary perspective view of the surgical tool of FIG. 1;

FIGS. 7A1-7A9 illustrate a Cardan type first driver of the transmission;

FIGS. 7B1-7B4 illustrate the Cardan drive of FIG. 7A, and also include the output of the first driver and the input of the second driver;

FIG. 9 is a fragmentary side elevation view of a drive transmission as seen in FIG. 5;

FIG. 14 is an exploded fragmentary perspective view of a portion of the drive transmission shown in FIG. 13;

FIG. 15 is a fragmentary perspective view of portions of the drive transmission of FIG. 13;

FIG. 16 is a fragmentary perspective view of portions of the drive transmission of FIG. 13;

FIG. 19 shows a fragmentary perspective view of another embodiment of a drive transmission with a drive rack in a first rotated position;

DETAILED DESCRIPTION OF THE INVENTION

Figure 3:
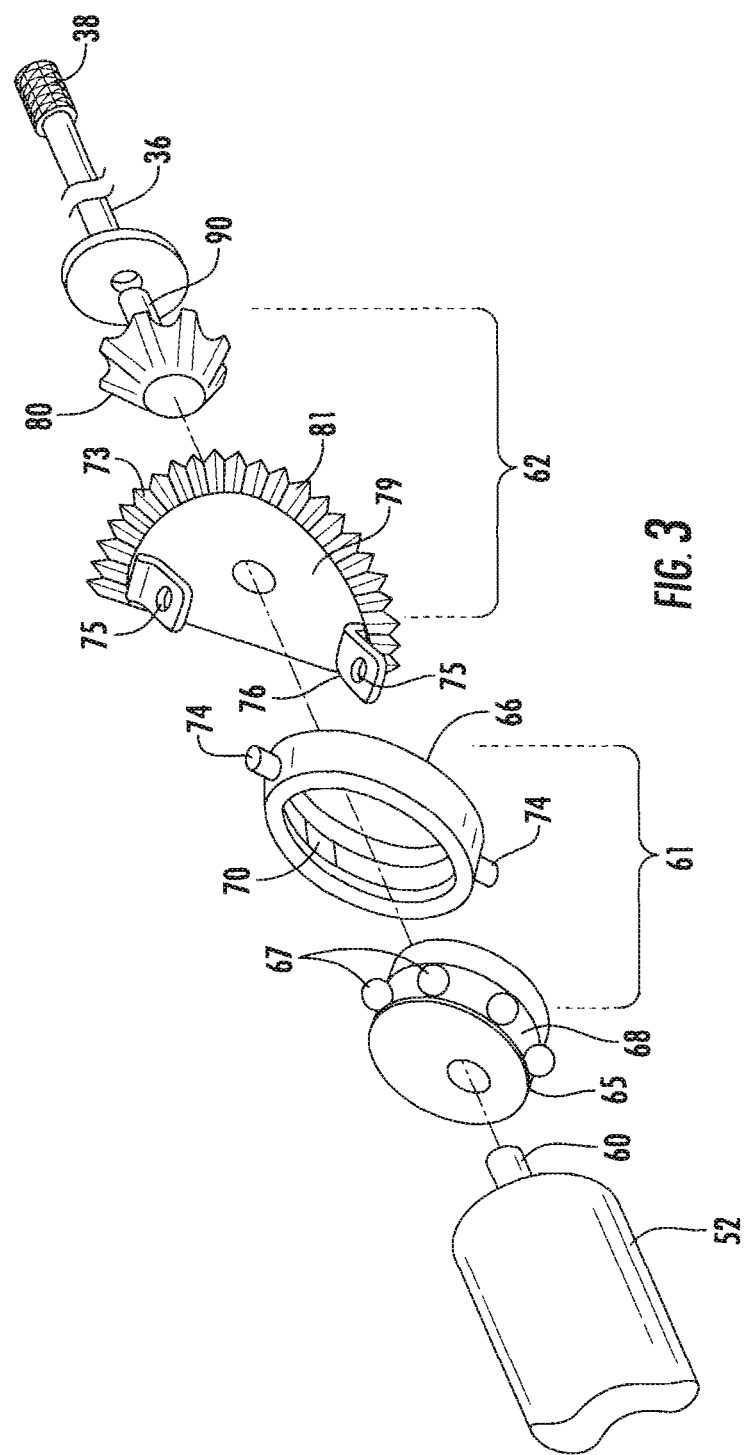
FIG. 3 is an exploded perspective view showing details of the internal parts of the surgical tool shown in FIG. 1.

The reference numeral 30 designates, generally, a rotary oscillating and reciprocating surgical tool useful, particularly, in the modification and/or removal of hard tissue such as bone, cartilage and disc. The surgical tool 30 is a handheld tool with a housing 32 providing a handle 34 for manually gripping the tool 30 for use during a surgical procedure. While one shape and style of handle 34 is illustrated, any suitable shape and style of handle can be provided. For example, a right angle pistol grip may be added. Additionally, the housing may have a narrow front portion for a smaller pencil-like "precision grip", while the larger remaining portion is sized to balance in the user's hand, such as in the web area between the index finger and thumb, for allowing better control with less fatigue.

The tool 30 can be used in surgical operations such as spinal surgery, wherein tissue such as bone, cartilage and disc material that is preferably of a non-fibrous tissue type may be modified or removed, such as from the spine of a patient. The tool 30 has an output shaft 36, which is driven to rotate in an oscillating manner of two alternate directions about the longitudinal axis of the shaft 36 by a drive transmission 35 that has two drive components, including an oscillation effecting first driver 37. Shaft 36 is provided with a cutting tool 38 positioned and secured to a distal end portion of the shaft 36. The cutting tool 38 is driven to rotate in alternate directions (oscillation) like the shaft 36, with a limited range of angular displacement of rotation, for example, between about 90° and about 180°. It has been found that such oscillatory rotation is effective in cutting or modifying hard tissue like bone, cartilage and portions of discs. It has also been found that this oscillatory rotation reduces the risk of damage to fibrous tissue such as muscle and nerve. The tool 30 is provided with the transmission 35 that includes the driver 37 to effect the oscillating rotation of the shaft 36 and its attached cutting tool 38. The transmission 35 is preferably provided with a reciprocation effecting second driver 39 coupled to the first driver 37 to simultaneously effect reciprocating motion of the shaft 36 and cutting tool 38 while they are oscillating. The second driver 39 uses the oscillating output of the first driver 37 to add the reciprocating motion to the shaft 36 and cutting tool 38. Reciprocating movement is parallel to the longitudinal axis of the shaft 36. The first driver 37 is upstream operationally of the second driver 39.

The tool 30 can receive energy for its operations from an external supply, such as a direct current power supply cord 40. A power control switch 42 can be provided on the housing 32 for controlling the operation of the tool 30, such as in an ON and OFF manner and/or in a variable speed manner. A light source 44 may also be provided on the housing 32 for illuminating the surgical site. Such a light source may be a light emitting diode (LED), which can be powered directly or indirectly by energy from cord 40. Energy can also be provided by a battery 46 or other energy storage device.

FIG. 2 illustrates internal components of the tool 30. An energy source can be provided by a battery supply 46 mounted in the housing 32. The battery supply 46 can be charged by the power cord 40. Electronics 48 are provided in the housing 32 for controlling the operation of the tool 30. A plurality of indicator lamps 50 may also be provided on the housing 32 and can be LEDs for indicating operational characteristics of the tool 30, such as the state of charge of the battery supply 46. Alternately, the batteries 46 can be eliminated in favor of the cord 40 being connected to a source of electrical energy. Preferably, the power supply is low voltage, e.g., 12 volts. Additionally, the motor 52 can be powered by compressed air, a vacuum, or any other suitable source of energy that would, on demand, effect rotation of a rotor portion of the motor 52.

The motor 52 is suitably mounted in the housing 32, wherein a portion of the motor, a rotor (not shown), is free to rotate and ultimately drive the shaft 36. A portion of the motor 52 is fixed against rotation in the housing 32 as is known in the art; for example, a motor housing and/or stator. The motor 52 drives the shaft 36 through the transmission 35 and its drivers 37, 39. The first driver 37 is operable for converting continuous rotary motion from the motor 52 to rotary oscillation of the shaft 36. The second driver 39 is operable for converting continuous oscillation from the first driver 37 and continuous rotation of the motor 52, and adds continuous reciprocating longitudinal movement to the shaft 36. The shaft 36 is suitably mounted in the nose 57 of the housing 32, as in one or more bearings 59. Operationally, the first driver 37 is upstream of the second driver 39. The journal bearings 59 need to accommodate both rotary and linear movement of the shaft 36, and a suitable bearing is a journal bearing. The shaft 36 may be angled relative to the longitudinal axis of the housing 32, as depicted in FIG. 1, for ergonomics. Cooling fins, or a cooling fan, (not shown) may be attached to or near the motor 52 for cooling the motor and/or the tool 30.

FIGS. 3-18 illustrate different forms of drivers 37 and 39.

Figure 4:
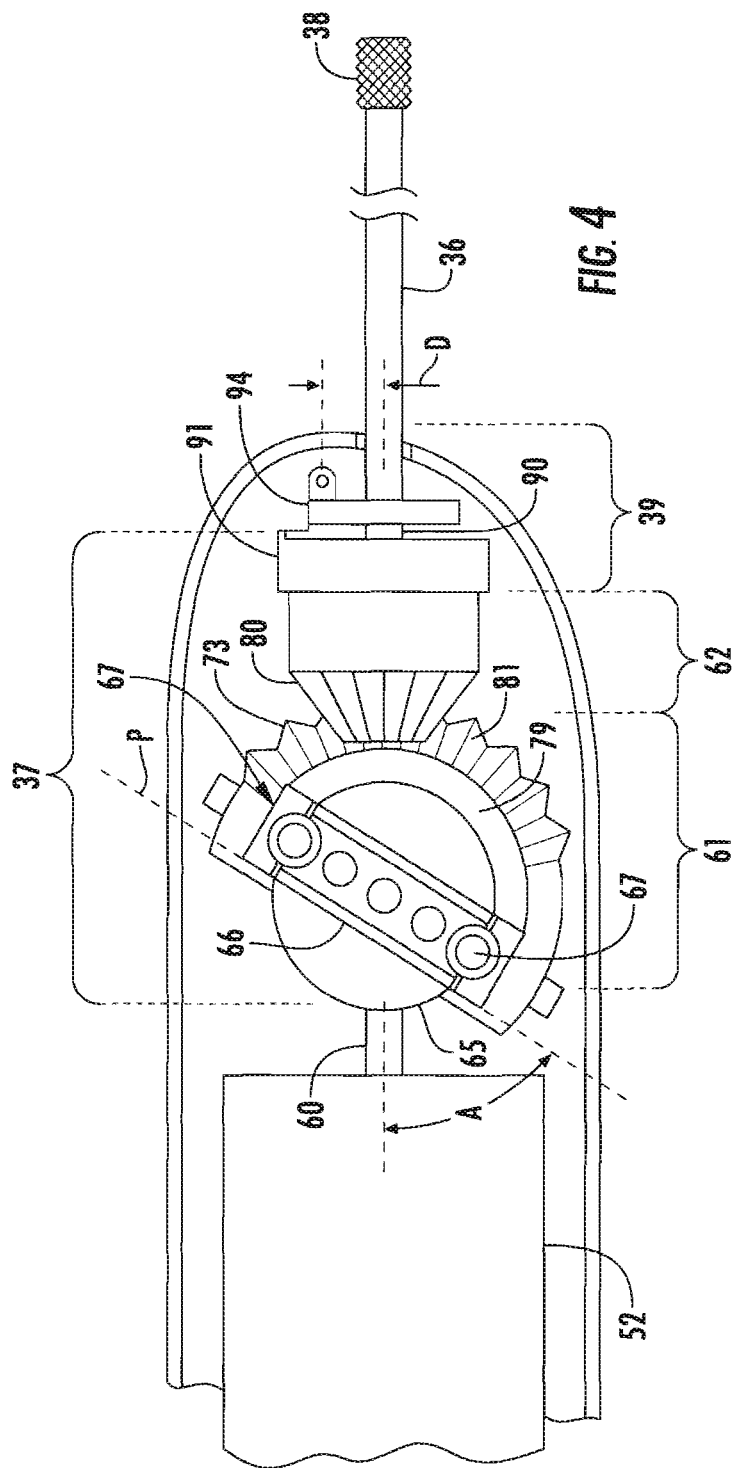
FIG. 4 is a top plan view of the details of the internal parts of the surgical tool shown in FIG. 1.
Figure 5:
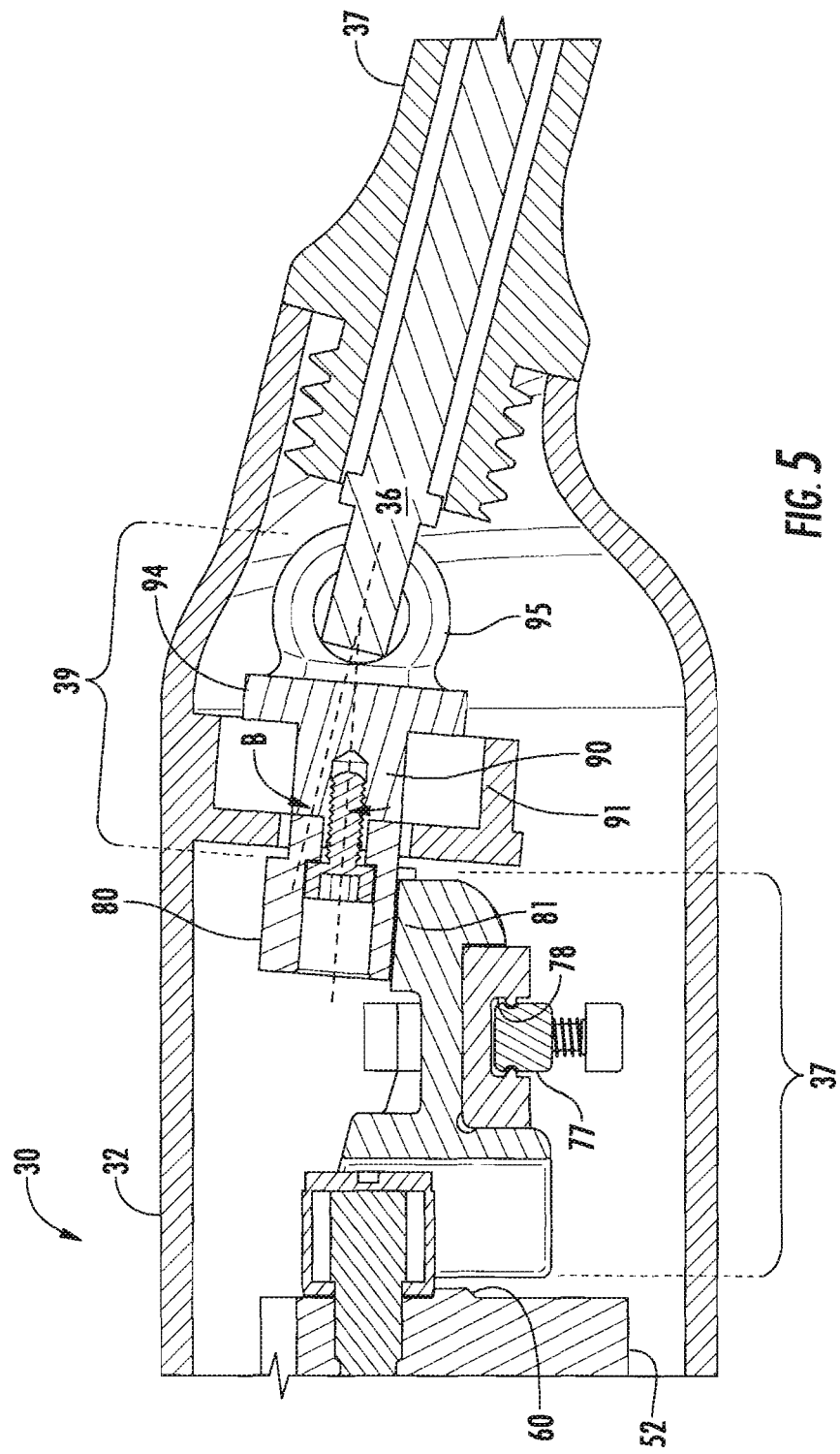
FIG. 5 is a fragmentary side view showing two drivers in the surgical tool shown in FIG. 1.

The first driver 37, as best seen in FIGS. 3-4, is positioned in the housing 32 and operably couples the second driver 39, and hence shaft 36, to the motor 52, and is operable to convert the continuous rotary motion of the shaft 60 of the motor 52 to oscillating rotary motion of the shaft 36. By oscillating rotary motion, it is meant that the shaft 36 will rotate a portion of a complete revolution first in one rotation direction and then in the other rotation direction, first counterclockwise, then clockwise, then counterclockwise again and so on. To effect this movement, the transmission 35 comprises the two driver components 37, 39. The first driver 37 is operable to convert the rotary motion of the shaft 60 of the motor 52 to oscillating rotary motion of the shaft 36, and the second driver 39 is operable to convert that oscillating motion to reciprocating linear motion while maintaining the oscillating motion.

In the illustrated embodiment, the first transmission driver 37 includes a ball bearing having an inner race 65, an outer race 66 and a plurality of bearing balls 67 contained in the races 65, 66. The inner race 65 is secured to the motor shaft 60 for rotation thereby about the central axis of the motor shaft 60. In the illustrated embodiment, the inner race 65 is in the form of a sphere, with a groove 68 therein, and sized to receive and retain the balls 67 therein. The outer race 66 is in the form of a ring, having a groove 70 recessed in the inner surface thereof, and sized to receive and retain the balls 67 therein. The grooves 68, 70 open toward one another and are positioned in a plane P that is set at an angle A relative to the longitudinal axis of the motor shaft 60. The angle A is the smallest angle between the plane P and shaft axis since the angle of the plane P relative to the shaft axis changes depending on the position from which the measurement is taken. The angle A is in the range of between about 30° and about 80°.

The outer race 66 is coupled to an oscillating connector 73, as for example with a pair of opposed pivot pins 74 projecting outwardly from the outer race and each being received in a respective bore 75 in a respective boss 76. The connector 73 is restrained in movement to a plane. In one example, a guide 77 (FIG. 5) is secured to the housing 32. The guide 77 is curved, and is received in a similarly curved slot 78 cooperating with the driver 37. Thus, the outer race 66 can only move in an oscillating manner, as can the connector 73. Another means to mount the connector 73 is with a pivot pin secured to the housing 32 and extending through a web portion 79 of the connector 73, which allows the connector 73 to rotate in an oscillating manner. The illustrated connector 73 has a curved gear rack portion 81, preferably a sector gear, coupled to the web 79 and carried thereby. A gear or gear segment, herein a gear 80, such as a bevel gear, engages the rack portion 81 of the driver 73 and itself is driven in an oscillating manner by rotation of the inner race 65 as driven by the motor 52. The gear 80 is coupled to the shaft 36 by the second driver 39 to effect driving of the shaft 36 in an oscillating manner.

The angle A determines the degree of rotation of the gear 80, and the rotational speed of the motor 52 determines the oscillation rate of the gear 80.

Figure 6A:
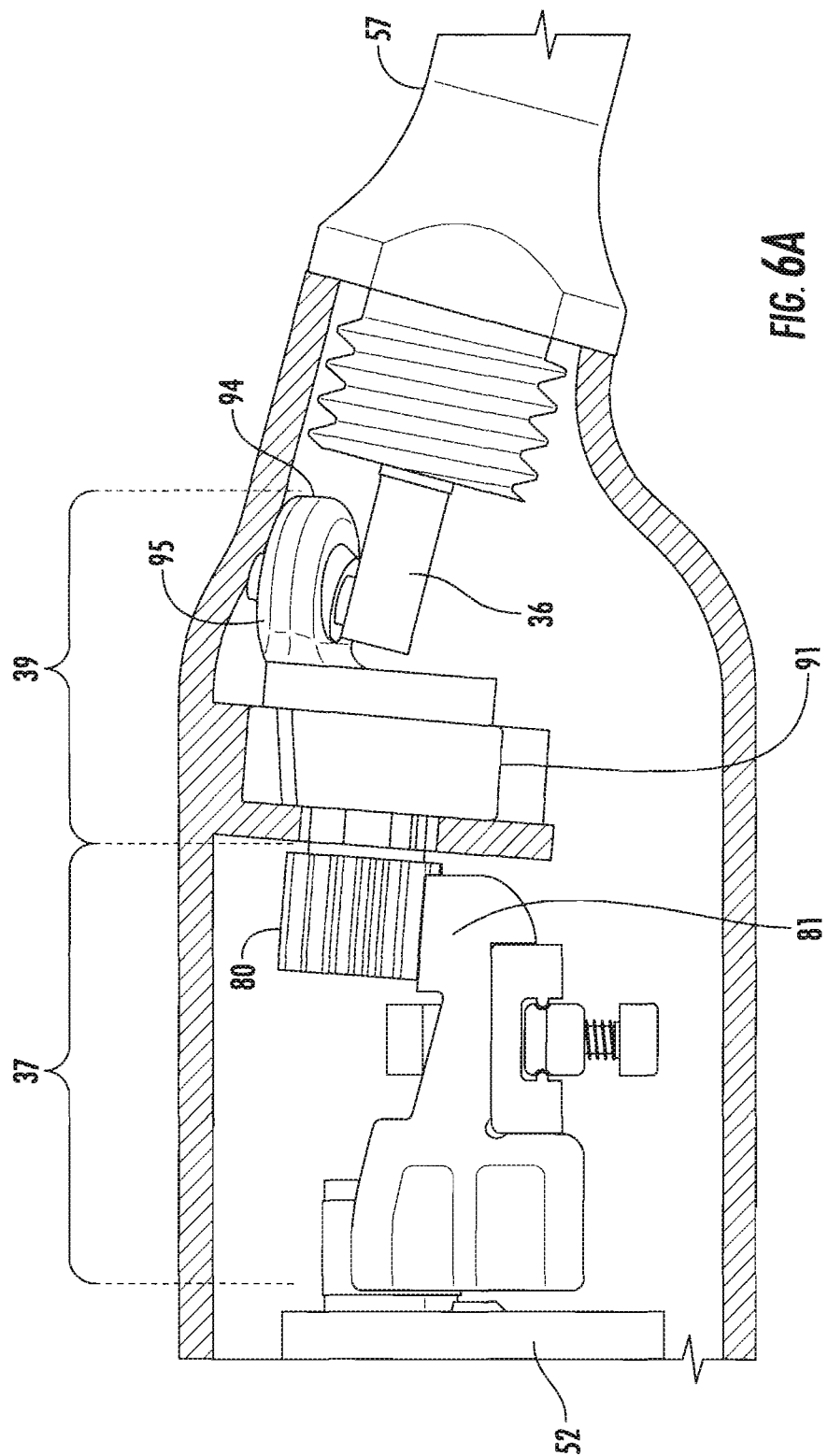
FIGS. 6A-6C illustrate various rotary positions of components of the second driver in the surgical tool that effect reciprocating movement of the cutting tool.
Figure 6B:
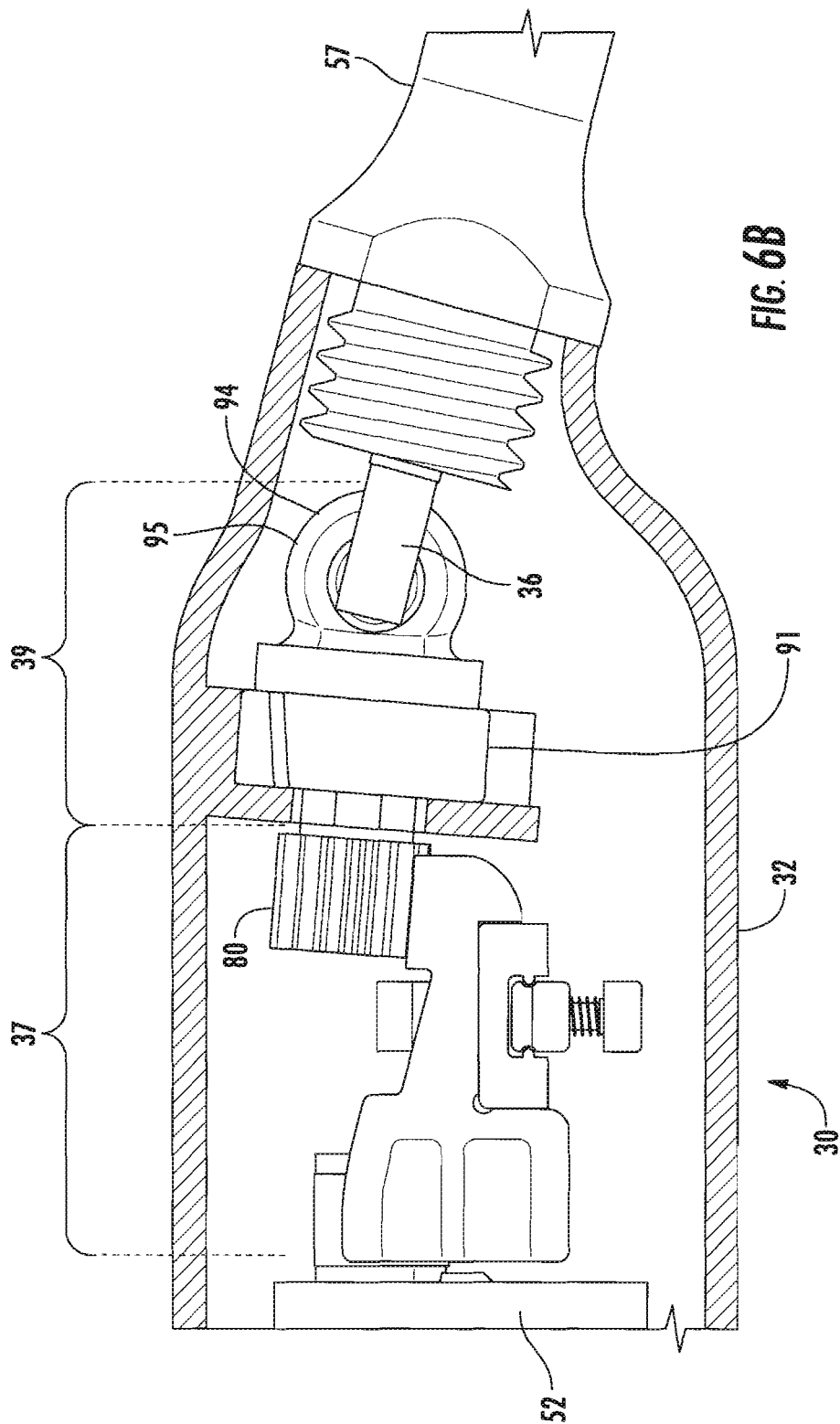
Figure 6C:
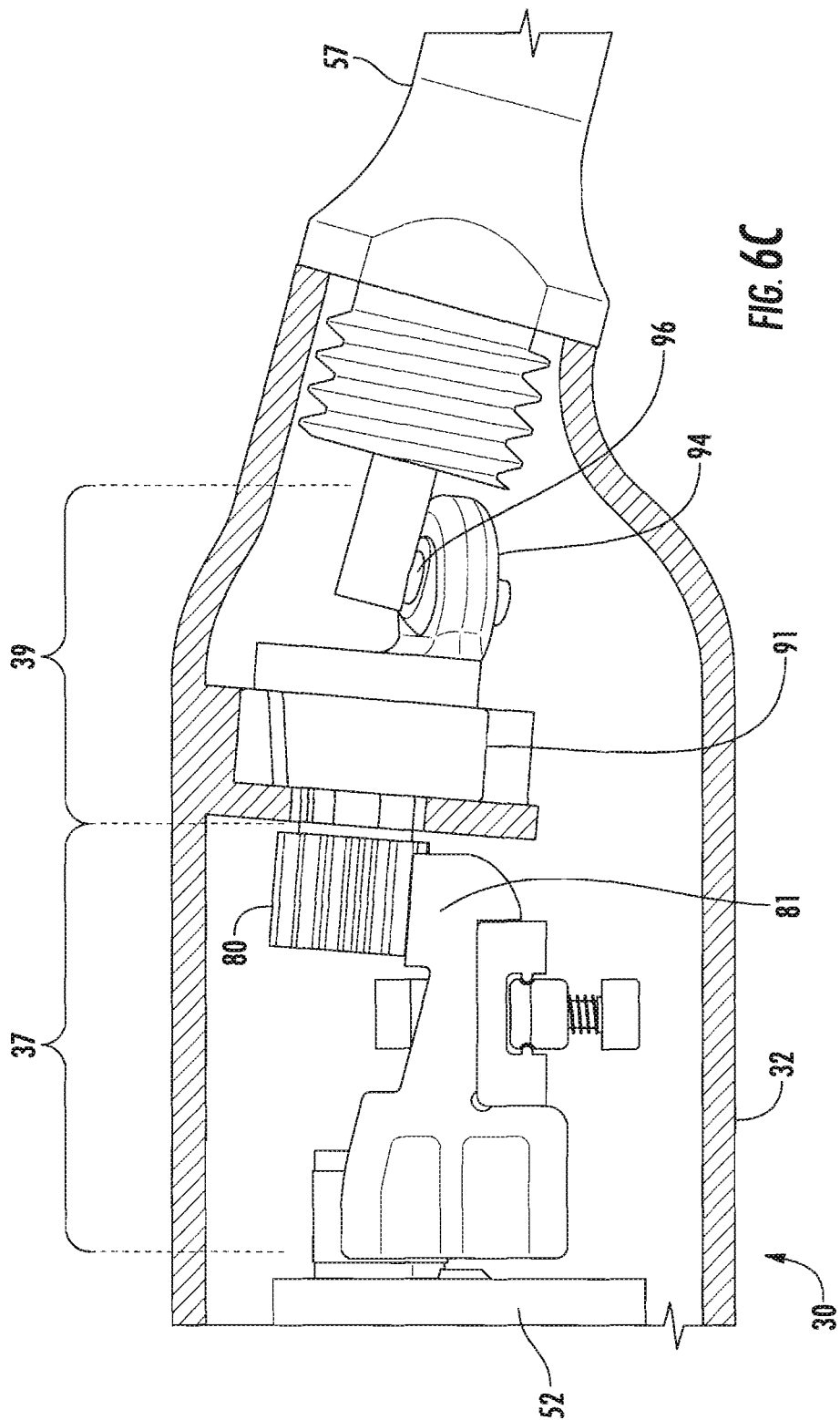

The gear 80 is part of the second driver 39, and is coupled to the shaft 36 to effect motion of the shaft 36 and associated cutting tool 38 as described herein. As shown, the gear 80 is fixed to a shaft 90 that is rotatably mounted to the housing 32 via a suitable bearing 91 fixed in position in the housing 32. The gear 80 is maintained in driving engagement with the rack 81, which oscillates along a curved path during operation of the motor 52. The shaft 36 is secured to a reciprocation effecting joint 94 in a manner allowing part of the joint 94 to pivot during rotation of the joint 94 and shaft 36. See FIGS. 6A-6C. Oscillation of the shaft 90 and the joint 94 effects oscillation of the shaft 36. The longitudinal axis of the shaft 90 intersects the longitudinal axis of the shaft 36, FIGS. 4, 5, and the axes are positioned at an angle B relative to one another. By being positioned at an angle B, which is preferably in the range of between about 5° and about 45°, the shaft 36, during oscillating rotation, will move longitudinally in two directions, effecting reciprocal movement of the shaft 36 and cutting tool 38 during their oscillating movement. To allow for both oscillation and reciprocation, the shaft 36 can be mounted in one or more journal bearings 59 fixed in position in the housing 32 and/or nose 57. The joint 94 acts as a wobble plate because of the angle B. Additionally, to effect the reciprocating movement, the shaft 36 is secured to the joint 94 at a position offset radially outwardly from the center of its rotation, the center of the shaft 90, FIGS. 4, 6A. This offset dimension D also determines the amount of reciprocating movement of the shaft 36. In a preferred embodiment, the joint 94 oscillates about 180° and starts at a rotational position, where the shaft 36 is at its most retractable position and ends at its most extendable position. The joint 94, as shown, includes a tab 95 on which is mounted a ball or spherical bearing 96. The shaft 36 is coupled to the bearing 96 as with a pin 98, FIG. 8. FIGS. 6A-6C illustrate the joint 94 in three different rotary positions and three different reciprocating positions. In FIG. 6A, the shaft is in its most extended reciprocating position. FIG. 6B shows the shaft 36 in an intermediate extended position. FIG. 6C shows the shaft 36 in its most retracted reciprocating position.

Figure 10:
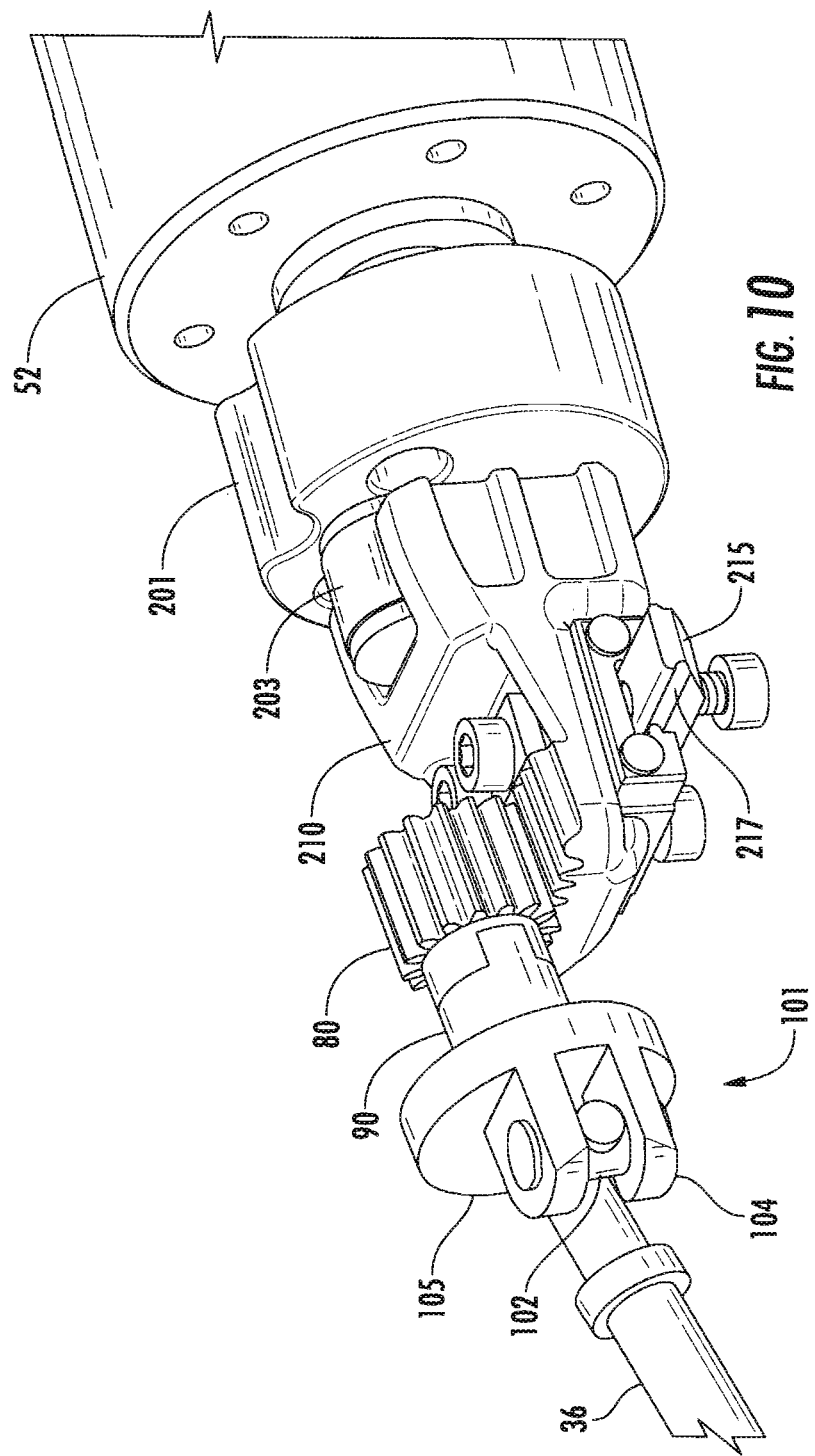
FIG. 10 is a fragmentary perspective view of a drive transmission similar to that shown in FIG. 8.

FIG. 10 illustrates another embodiment of connecting the shaft 36 to the second driver 39. The reciprocating effecting joint 101 is used instead of the joint 94. A pivot pin 102 is mounted for rotation in a clevis 104, which in turn is mounted to a crank member 105. The crank member 105 is mounted to a shaft 90, which is rotatably mounted in the bearing 91 as described above. The shaft 36 is secured to the pivot pin 102. This form of joint 101 is similar in operation to the joint 94 as described above.

Figure 11:
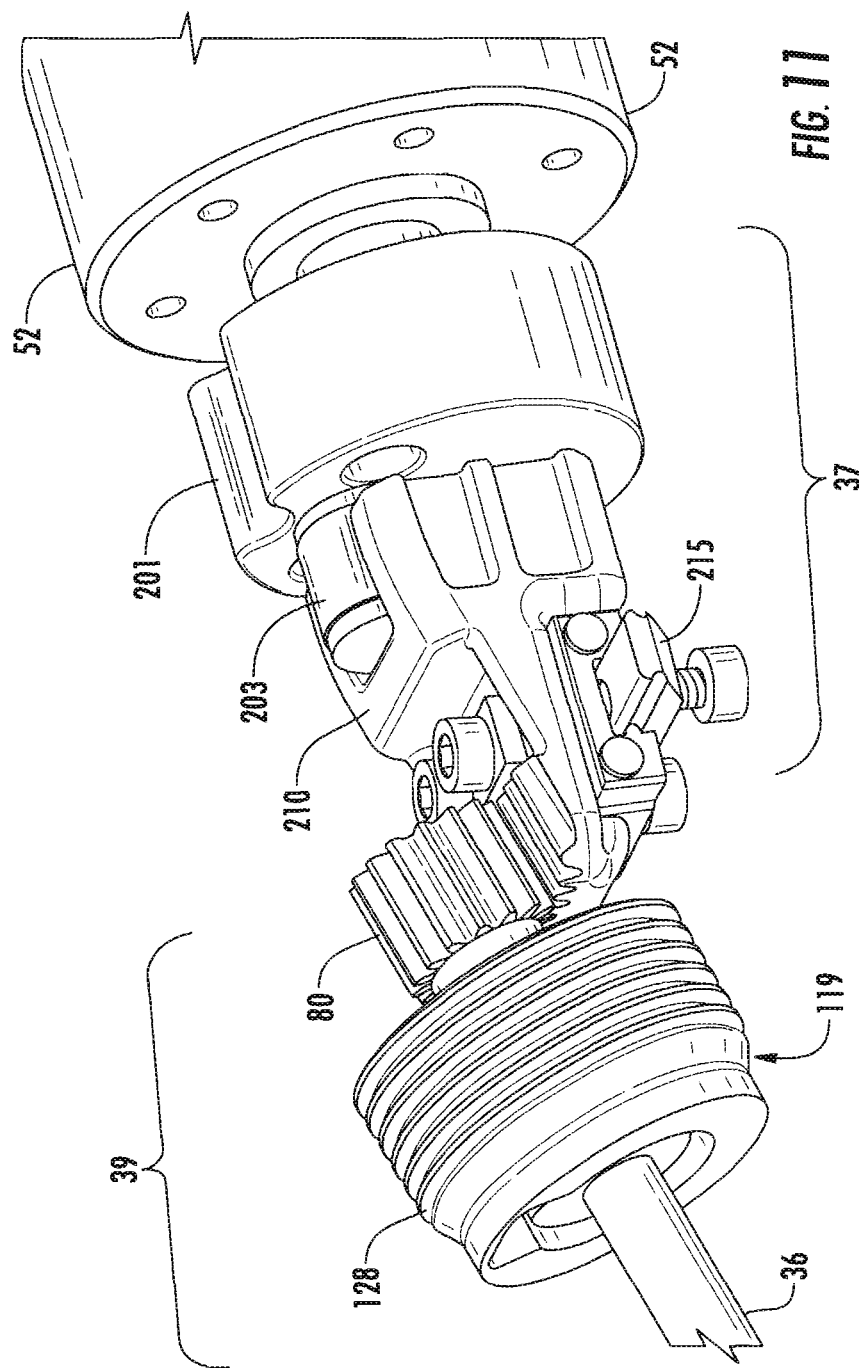
FIG. 11 is a fragmentary perspective view of another embodiment of a drive transmission similar to that shown in FIG. 8, but with an alternate second driver.
Figure 12:
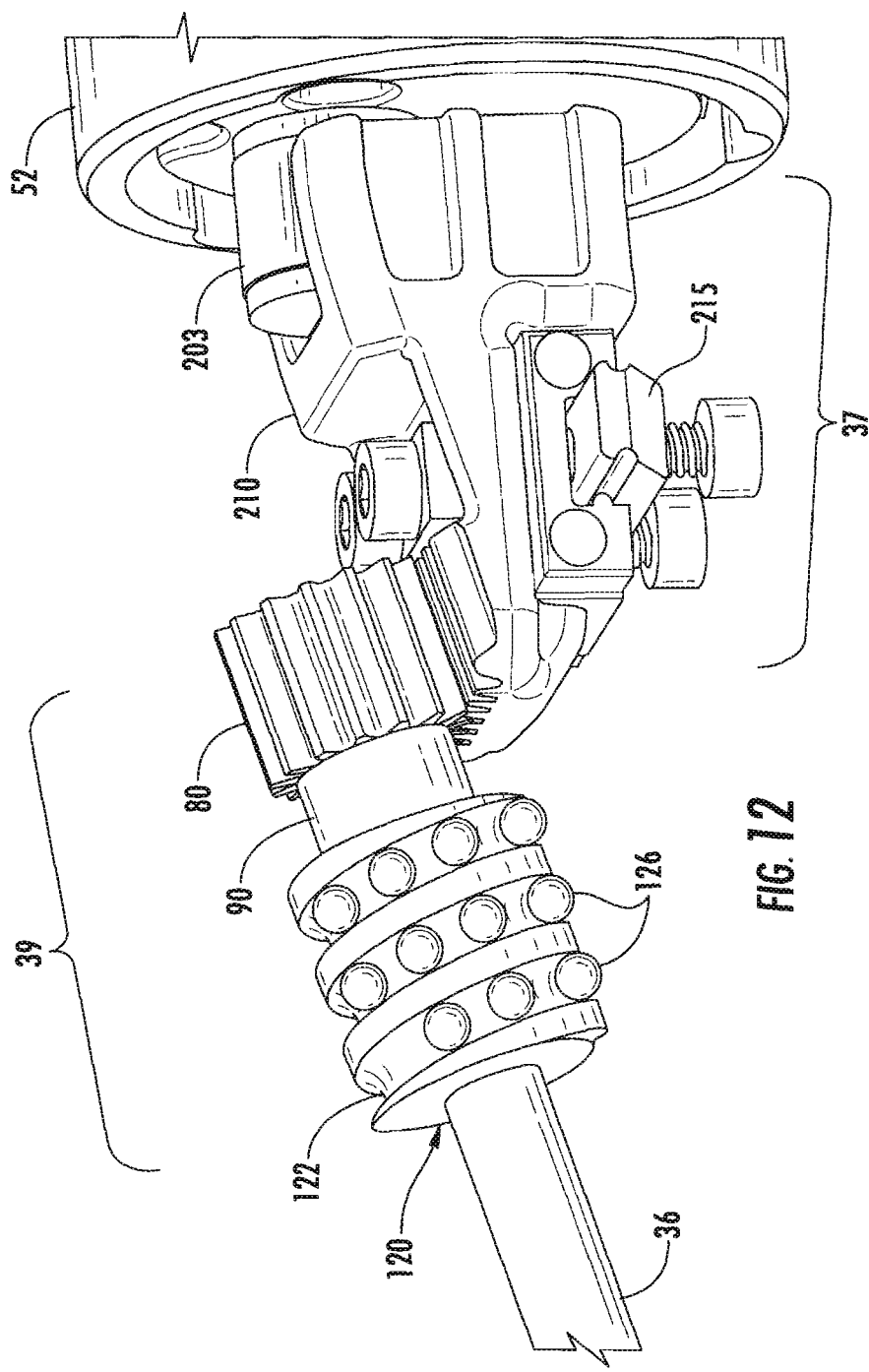
FIG. 12 is a fragmentary perspective view of a drive transmission showing details of parts in FIG. 11.

FIGS. 11, 12 illustrate another embodiment of a second driver 39 that is operable to effect longitudinal reciprocating movement of the shaft 36. The shaft 36 is coupled to the shaft 90 relative to longitudinal movement therebetween, as for example, by the use of a spline connection, as can be seen in FIG. 14. An inner bearing race 120 is secured to the shaft 36 and has an outwardly opening helical bearing groove 122. A plurality of bearing balls 126 are contained within the groove 122. An outer bearing race 128 is mounted in the housing 32 or nose 57 and is fixed against movement relative thereto. The outer bearing race 128 has a helical groove (not shown) that opens inwardly and contains the bearing balls 126 therein. When the shaft 36 rotates in an oscillating manner, as effected by the first driver 37, the shaft 36 will move in a longitudinal reciprocating manner by cooperation between the inner and outer bearing races 120, 128, respectively, via the bearing balls 126. This forces the inner race 120 to move longitudinally in a reciprocating manner.

Figure 13:
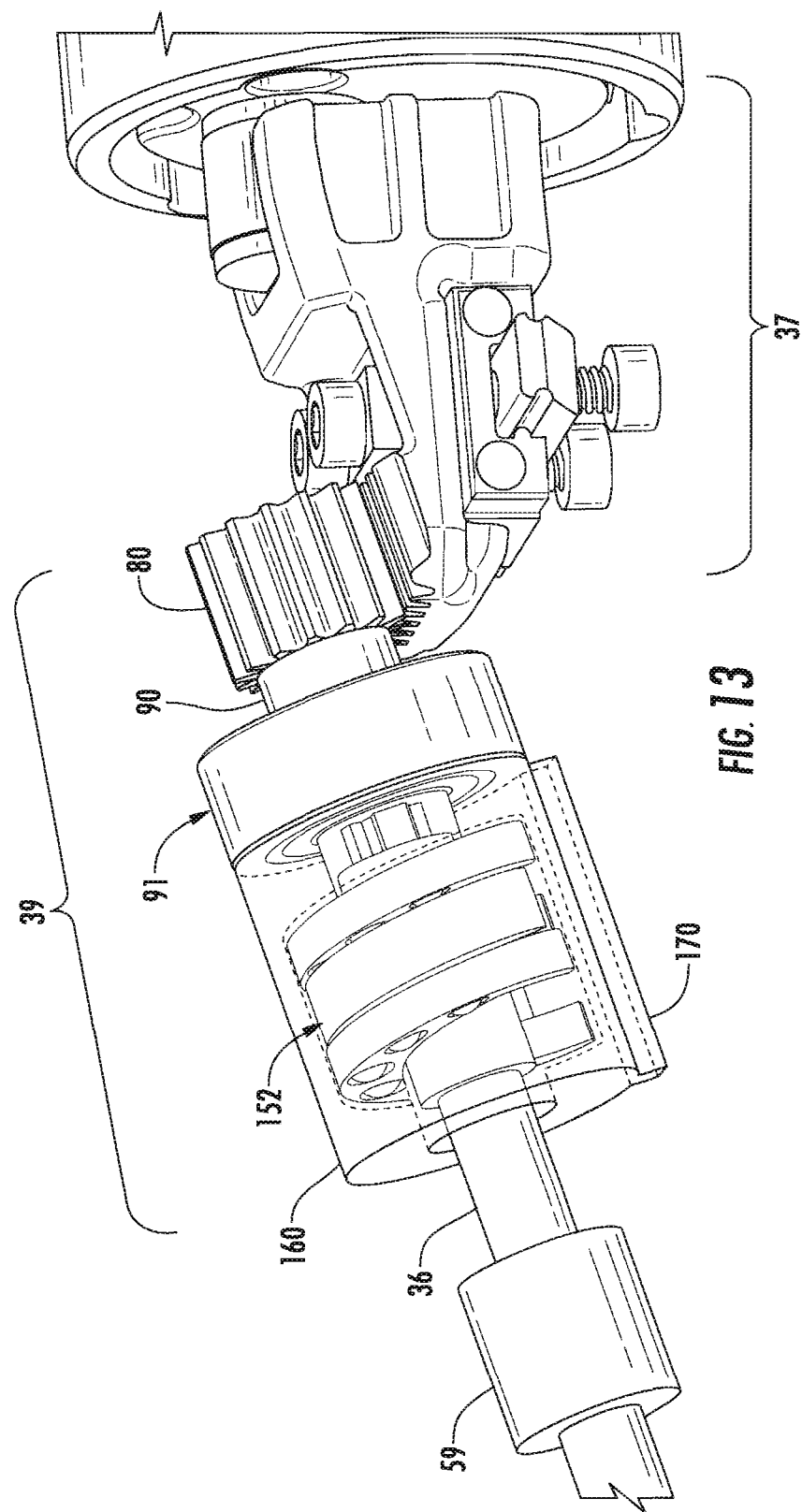
FIG. 13 is a fragmentary perspective view of another embodiment of a drive transmission.
Figure 17:
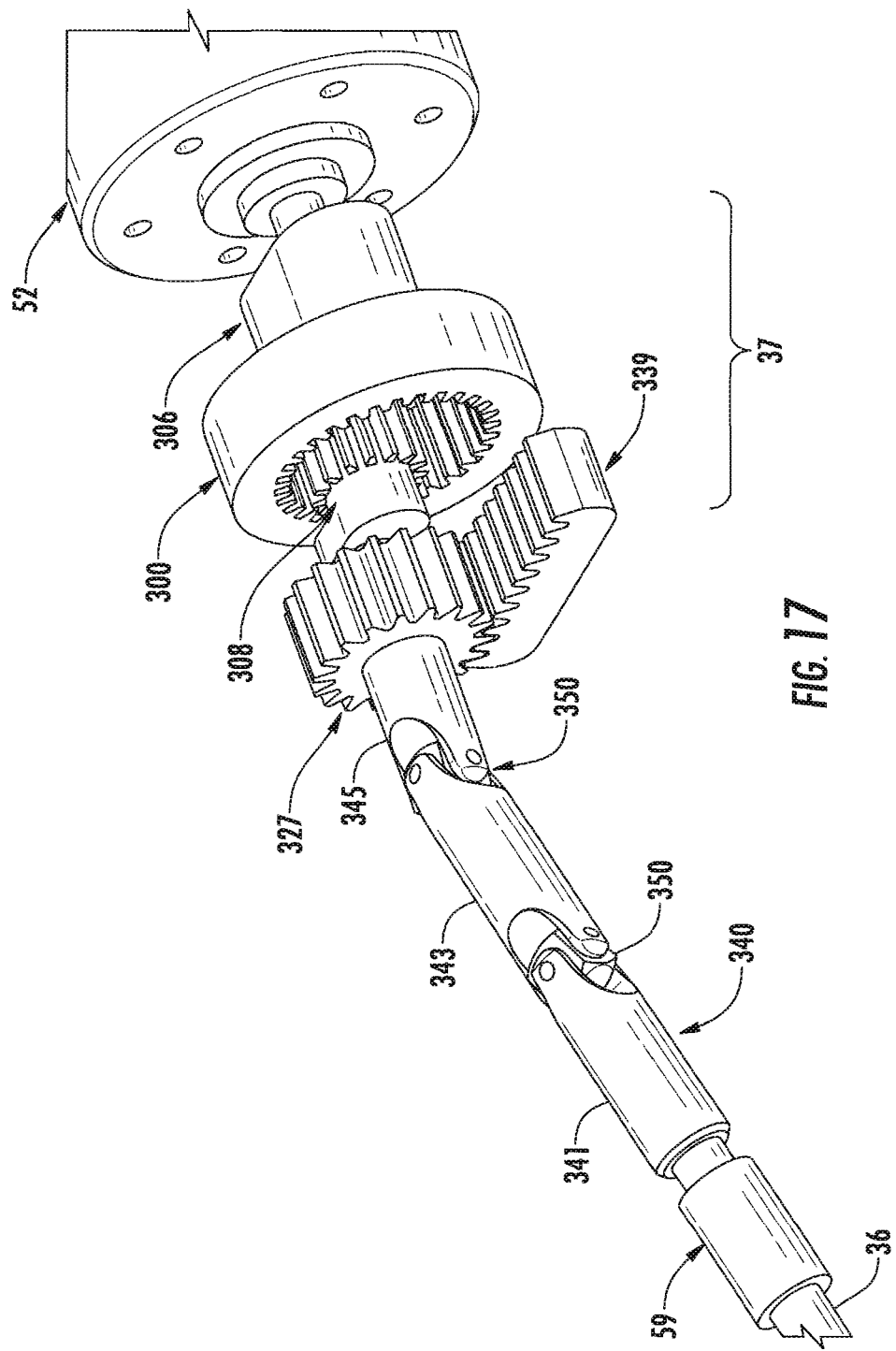
FIG. 17 is a fragmentary perspective view of portions of a still further embodiment of a drive transmission.
Figure 18A:
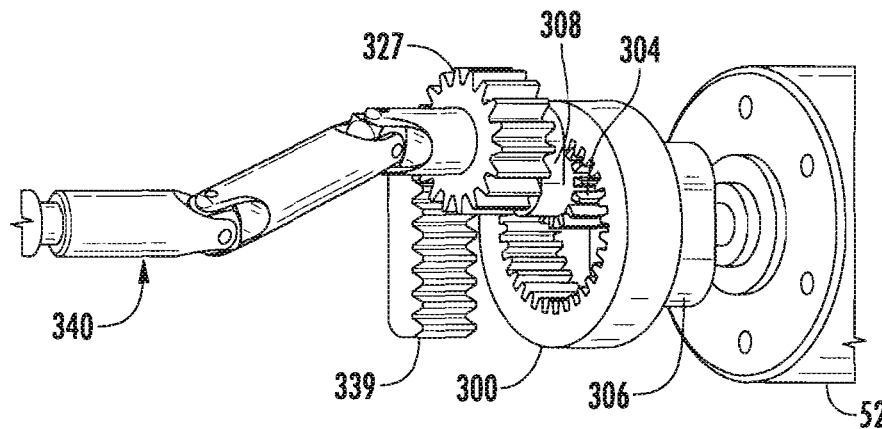
FIGS. 18A-18D are fragmentary perspective views of portions of the transmission of FIG. 17 showing sequential positions of portions of the second drive effecting reciprocating movement of a cutter shaft and associated cutter.
Figure 18B:
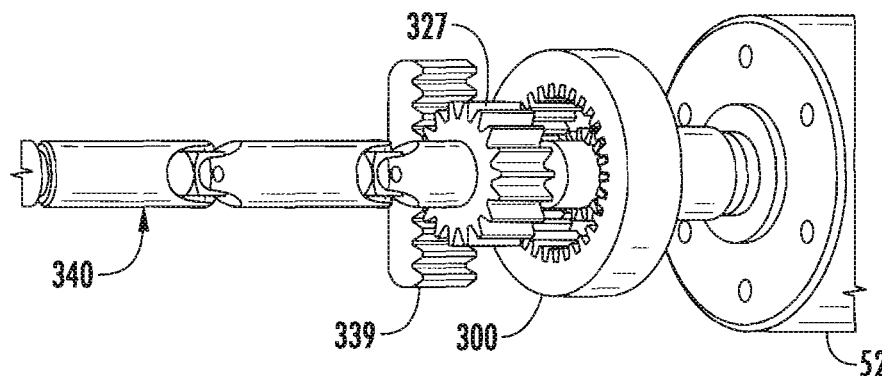
Figure 18C:
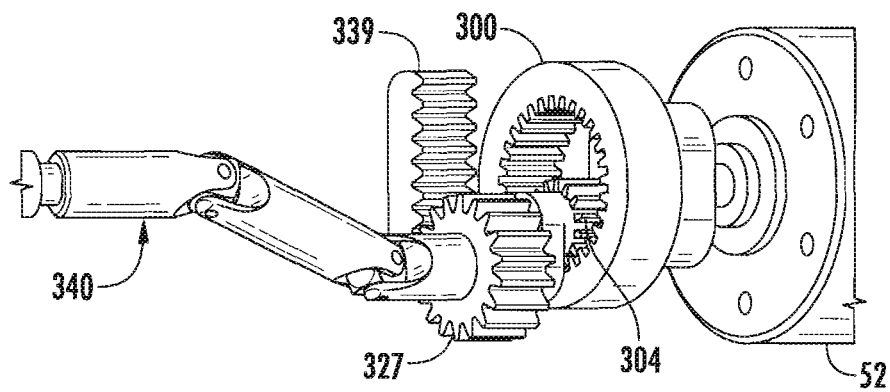
Figure 18D:
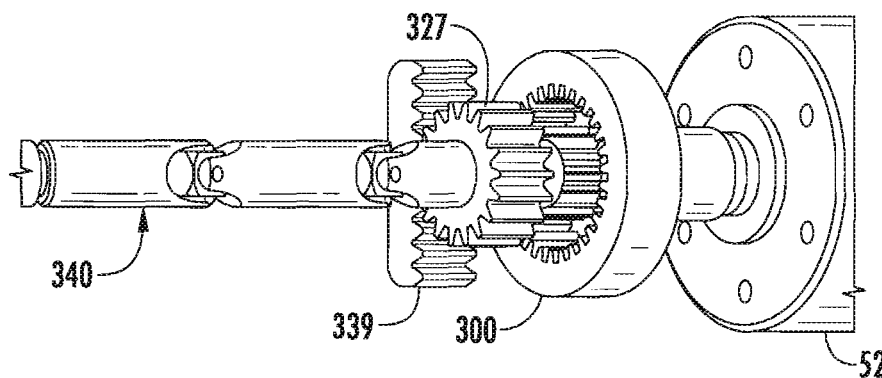

FIGS. 13-16 illustrate a further embodiment of a second driver 39 that is operable to effect longitudinal reciprocating movement of the shaft 36. This embodiment uses a helical bearing 152 to effect longitudinal reciprocating movement of the shaft 36 while the shaft 36 is being rotationally oscillated by the first driver 37. As seen in FIG. 14, the shaft 36 has its proximal end 154 male splined and is longitudinally movably received in a female splined socket 156 within the shaft 90. Thus, the shaft 36 can move both longitudinally and rotationally while being driven by the drivers 37, 39. The helical bearing 152 includes a split housing 160 having housing portions 160A and 160B. The housing 160 is mounted in the housing 32 and/or its nose 57 in a manner to prevent relative rotation therebetween. This can be accomplished, as seen in FIGS. 13, 14 by providing the housing 160 with a laterally projecting key 170. The bearing 152 has an inner race 172 secured to the shaft 36 and provides a radially projecting helically longitudinally extending flange 176. Bearing balls 178 are positioned on opposite faces 180, 181 of the flange 176. The helical bearing 152 is provided with a pair of outer races 184 that have a plurality of bearing ball receiving pockets 186 in the faces opposite the faces 180, 181. The outer races 184 retain the bearing balls 178 in contact with their respective face 180 or 181. Rotation of the outer races 184 relative to the housing portions 160A and 160B is limited by stop faces 190 on the outer races 184, and stop faces 192 on the inside of the housing portions 160A and 160B.

Figure 8:
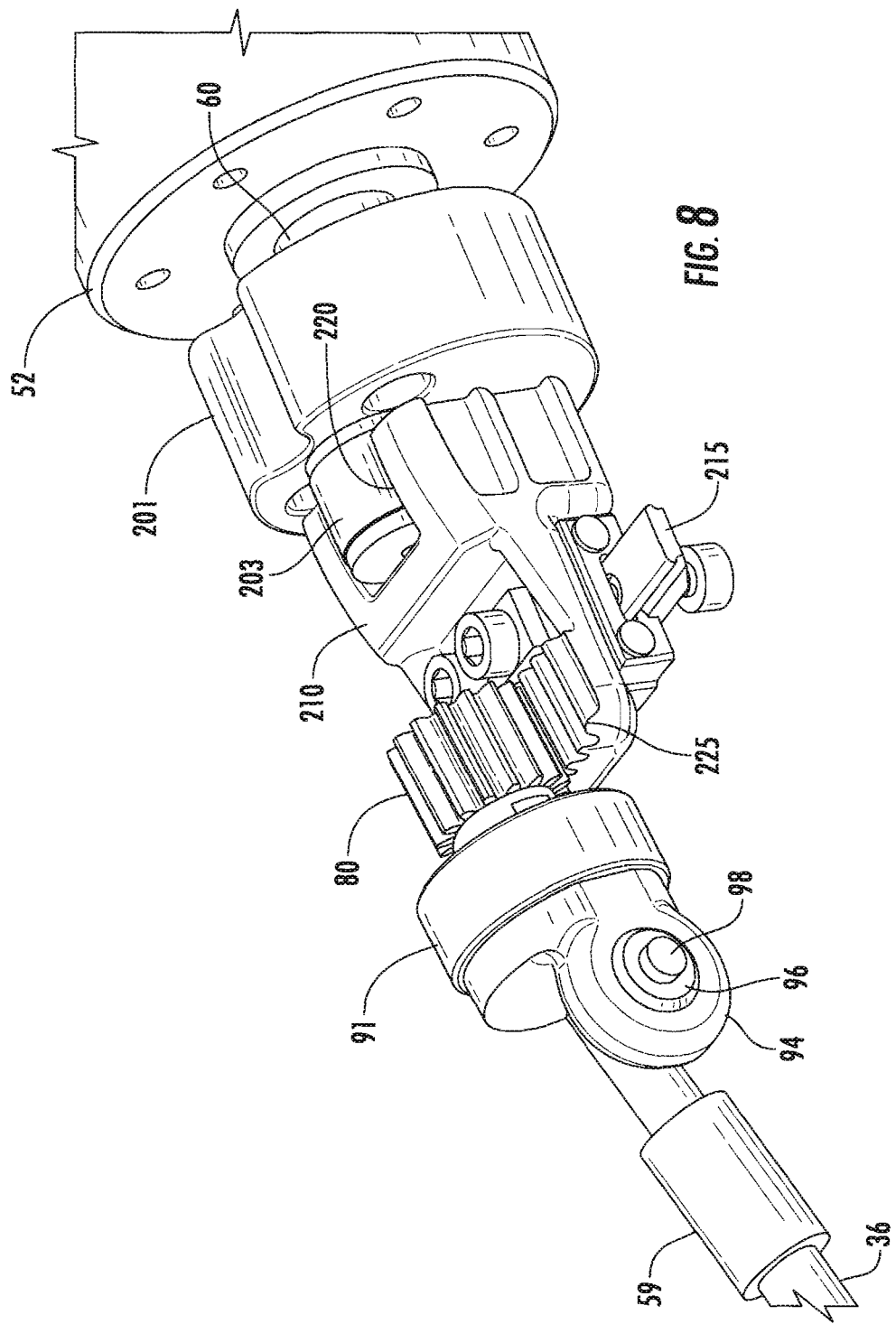
FIG. 8 is a fragmentary perspective view of one embodiment of a drive transmission.
Figure 9:
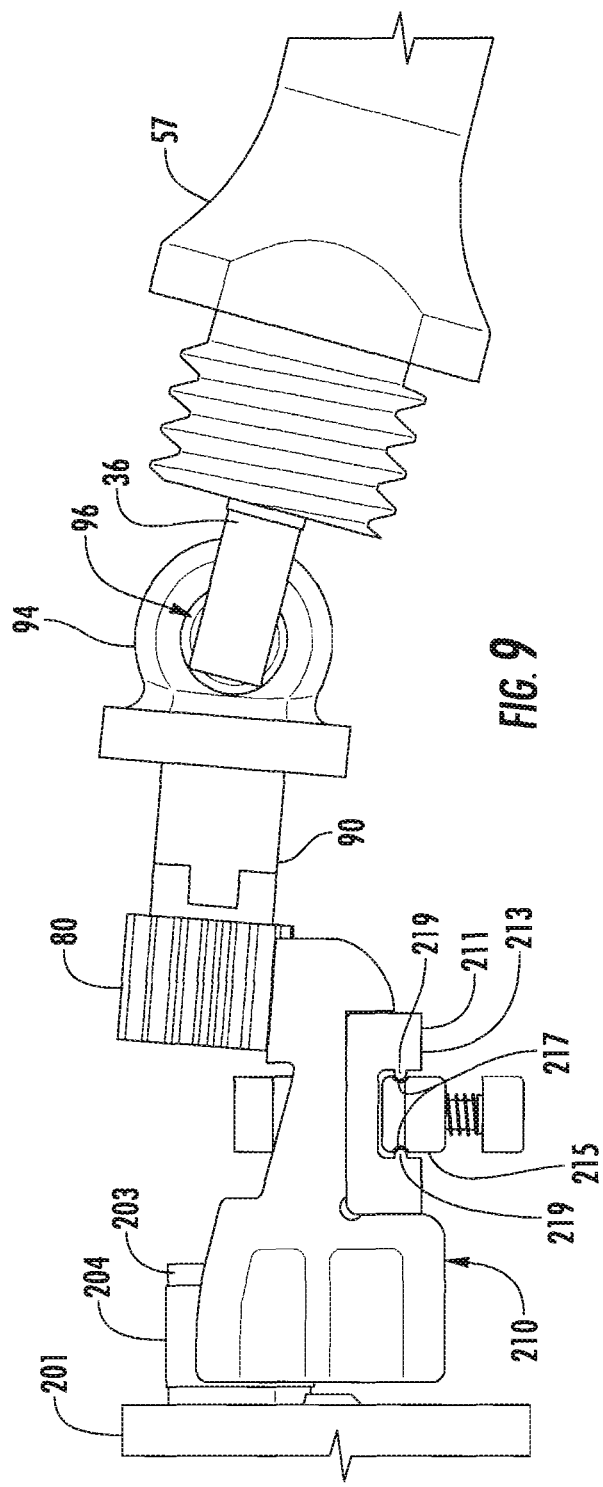

FIGS. 8, 9 illustrate a second embodiment of the first driver 37. It is similar to the driver 37 shown in FIGS. 5, 6A-6C. The motor 52 has a crank assembly 201 mounted on its output shaft 60. The crank assembly 201 includes a drive arm 203 that can include a wear resistant bearing member 204. The drive arm 203 is offset radially from the center of rotation of the crank assembly 201. Thus, rotation of the crank assembly 201 moves the drive arm 203 in a circular path. A follower assembly 210 is mounted in the housing 32 in a manner to restrict its movement in a plane laterally from side to side. As shown, a guide bed 211 is provided and includes a guide channel 213, which receives in it a guide rail 215. As shown, the guide rail 215 is coupled to the bed 211 to prevent their separation during movement. As illustrated, the guide rail 215 has a pair of opposed grooves 217 in each of which is received a respective guide rail 219 to provide guided restrained movement between the guide bed 211 and guide rail 215. The guide rail 215 is straight, thereby restricting movement of the follower assembly to linear movement in a plane. The drive arm 203 is received in a channel 220 with a close fit, whereupon revolving movement of the drive arm 203 will effect reciprocating lateral movement of the follower assembly 210. The follower assembly 120 is drivingly coupled to the second driver 39 in a manner to effect oscillating rotation of the shaft 36. As shown, a gear rack 225 is provided on the follower assembly 210 to mesh with the gear 80, whereby lateral movement of the follower assembly 210 effects oscillating rotation of the shaft 36, which, with operation of the second driver 39, will simultaneously effect reciprocating motion of the shaft 36.

FIGS. 7A, 7B illustrate another form of drivers 37, 39. The first driver 37 is illustrated as a Cardan type drive that is operable to effect rotary oscillation of the shaft 36. While the structure shown in these Figures effects only oscillating rotation, the additional structure shown in FIGS. 17, 18A-18D shows a mechanism to convert the oscillating rotation into oscillating rotation and linear reciprocation of the shaft 36.

FIG. 7A illustrates the basic functioning of a Cardan mechanism. An internal gear member 300 has an external gear 304 received therein. The gear ratio between the internal gear 300 and the external gear 304 is 2:1. The gear 300, in this case, is fixed against movement, while the gear 304 is part of a crank arm 306 mounted to motor 52. As the crank arm 306 effects revolving of the gear 304 about the center of rotation of the motor shaft, the gear 304 moves about the interior of the internal gear 300. The gear 304 has secured thereto an output arm 308 that has a center of rotation that is coaxial with the center of rotation of the motor 52 when the arm 308 is at its center position within the gear 300, as seen in FIG. 7A2-7A9. In this type of mechanism, the center of the arm 308 moves in a linear path in a laterally reciprocating manner. Thus, rotary output motion of the motor shaft can be converted into reciprocating linear motion. This can be seen in FIG. 17.

As seen in FIG. 7B, the Cardan style first driver 37 is coupled to a follower 320 that is operable to convert the linear movement of the arm 308 into oscillating rotary motion of the shaft 36. The illustrated follower 320 receives the arm 308 in an elongate slot (not shown) on the side facing the motor 52; this allows the arm 308 to move freely as the follower 320 pivots about a pair of pivot pins 322 that are mounted in suitable bearings (not shown) in the housing 32 and/or its nose 57. As the arm 308 moves laterally, as seen in FIG. 7A, it will force the follower 320 to pivot. A curved gear rack 325 is secured to the follower 320, is preferably integral therewith, and has the gear teeth spaced radially outwardly from the pivot pins 322. The radius of the gear rack 325 is substantially the radial distance of the gears from the center of rotation of the pivot pins 322. The gear rack 325 is meshed with a gear or gear segment 327, such as a spur gear that is secured to the shaft 36. As the follower 320 oscillates about its pivot pins 322, the shaft 36 is driven in a rotary oscillating manner.

FIGS. 17 and 18A-18D illustrate a still further embodiment of a second driver 39. It utilizes a Cardan first driver 37, such as shown in FIG. 7B. However, instead of a curved gear rack 325, this form uses a straight gear rack 339, and the gear 327 which is coupled to the shaft 36 moves laterally with its center of rotation being in a straight line. This can be accomplished by having the arm 308 centered on the center of rotation of the gear 304. The gear 327 is coupled to the shaft 36 through the use of a drive shaft 340. As shown, the drive shaft 340 has three sections 341, 343, and 345. Section 341 is secured to the shaft 36, which, in turn, is mounted in the bearing 59, as described above. Section 343 is coupled to section 341 in a manner that allows the axes of sections 341 and 343 to change their angular orientation. This can be accomplished by a universal joint (u-joint) 350. Section 343 is coupled to section 345 in a similar manner, as with a second universal joint 350. As the gear 327 rotates and moves laterally side-by-side on the gear rack 339, the length of the drive shaft 340 increases and decreases, effecting linear reciprocating movement of the shaft 36. This can be seen in FIGS. 18A-D.

Figure 20:
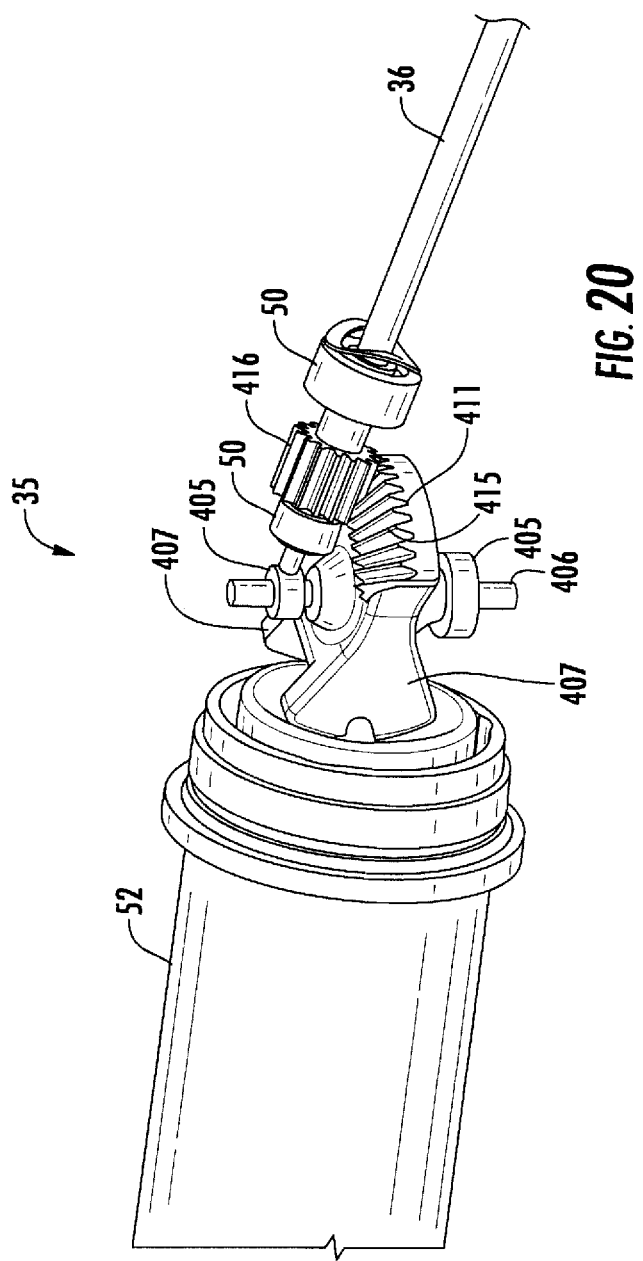
FIG. 20 shows a fragmentary perspective view of the drive transmission with a drive rack in a second rotated position.
Figure 21:
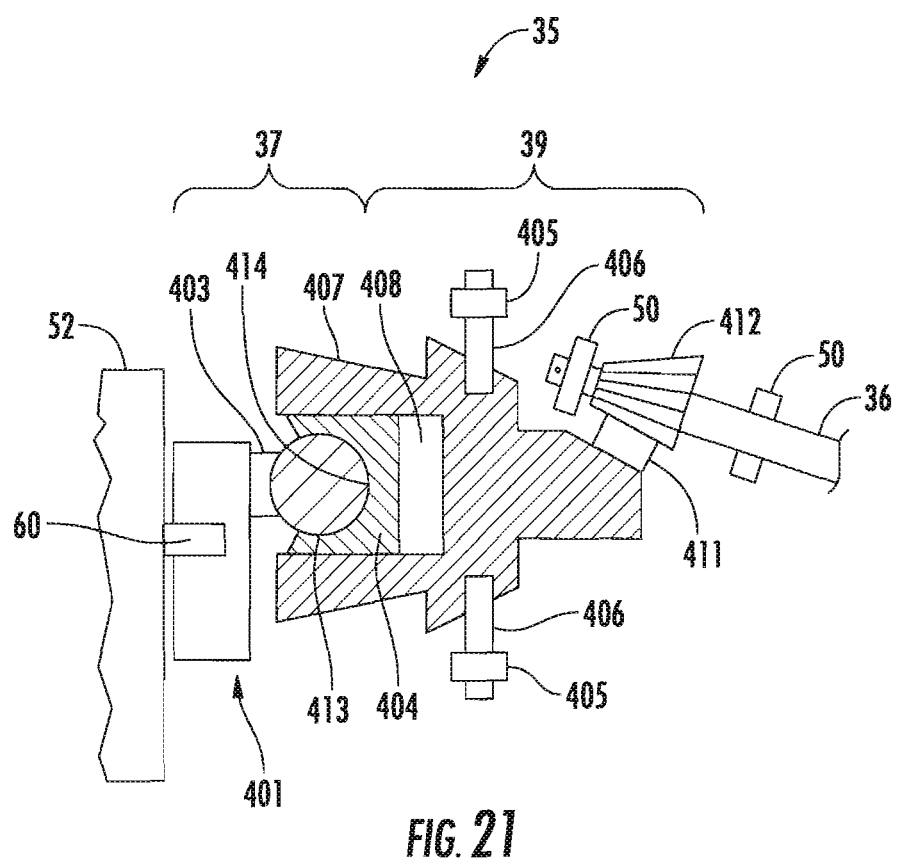
FIG. 21 is a side elevation view of the drive transmission of FIGS. 19, 20 with sections broken away to show details thereof.

FIGS. 19-21 illustrate another embodiment of the transmission 35, first driver 37 and second driver 39. The transmission 35 in FIGS. 19-21 is similar to that shown in FIGS. 5, 6A-6C in that it uses both a rack and pinion gear drive arrangement and a crank assembly. The motor 52, described above, has a crank assembly 401 mounted on its output shaft 60. The crank assembly 401 includes a drive arm 403 that can include a wear resistant bearing member 404. The drive arm 403 is offset radially from the center of rotation of the crank assembly 401. Thus, rotation of the crank assembly 401 moves the drive arm 403 in a circular path. A follower assembly 410 is mounted in the housing 32 in a manner to restrict its movement in a plane laterally from side to side in a pivoting manner about an axle arrangement 406. The axle arrangement 406 is mounted for pivoting movement of follower assembly 410 with suitable bearings 405 mounted in the housing 32. The follower assembly 410 has a pair of spaced apart arms 407, each with an inwardly opening channel 408 sized and shaped to receive the bearing member 404 therein. The channels 408 are portions of a cylinder and the bearing 404 is a cylinder, allowing the bearing 404 to move both longitudinally and rotationally relative to the follower assembly 410. The bearing 404 is mounted to the drive arm 403 in a manner to allow the drive arm to be rotated by the motor 52 and effect rotational pivoting movement of the follower assembly 410. As shown, the drive arm 403 is provided with a generally spherical bearing 413 mounted in a spherical cavity 414 in the bearing 404 that permits multi axis rotation of the bearing 413 relative to the bearing 404. The bearing 404 is in the form of a ball joint. When the drive arm 403 is driven so the bearing 413 moves in a circular path, the bearing moves longitudinally in the channels 408, as well as rotationally. The follower assembly 410 is provided with a gear rack 411 forward of the axle arrangement 406 from the arms 407. The rack 411 is preferably a sector gear and is preferably curved, having an inner edge curved in a circular arc with a radius approximately equal to its spacing from the center of rotation about the axle assembly 406 and an outer edge curved in an arc with a radius approximately equal to its spacing from the center of rotation about the axle assembly 406. The gear tooth surface 415 is beveled relative to the plane of rotation of the follower assembly 410. This accommodates its driving a pinion gear 416 mounted to the shaft 36 to which it is mounted. The gear 416 is a bevel gear that has gear teeth that mesh with the gear teeth of the rack 411. The shaft 36 is mounted in the housing 32 via bearings 50 as described above. The rack 411 rotates in two directions about the axle assemble 406 which effects oscillating rotation of the shaft 36, also in two directions. Thus, the follower assembly 410 converts one directional rotation of the motor 52 and drive arm 403 into two direction oscillatory rotation.

The term gear, bevel gear, curved gear rack and gear rack as used herein includes both complete gears and gear segments.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for removing bone comprising:
   providing a surgical tool having an oscillating cutter for cutting a bone, comprising:
   a housing;
   a motor mounted in the housing and having a rotatable output shaft;
   a cutter assembly having a cutter shaft carried by the housing, a cutter on a distal end of the cutter shaft and a gear disposed proximally of the cutter; and
   a first driver coupled to the output shaft and including:
      a crank coupled to the motor output shaft; and
      a crank bearing radially offset from a center of rotation of the crank;
   a second driver coupled to the first driver downstream thereof, the second driver including a follower assembly having:
      a follower having a pair of arms defining a channel and a gear rack in mesh with the gear of the cutter shaft; and
      a follower bearing disposed in the channel and receiving the crank bearing such that rotation of the crank bearing causes rotary oscillation of the follower;
   wherein rotary oscillation of the follower causes oscillating rotation of the cutter shaft gear,
   removing the bone using the surgical tool.

2. The method of claim 1, further comprising a drive arm coupling the crank to the crank bearing.

3. The method of claim 2, wherein the crank bearing is a spherical bearing.

4. The method of claim 1, wherein:
   the crank bearing is a spherical bearing; and
   the channel is cylindrical and circular for receiving the crank bearing.

5. The method of claim 1, wherein the follower assembly includes an axle pivotally connected to the follower between the channel and the gear rack.

6. The method of claim 5, further comprising a shaft bearing rotatably coupled to the axle and attached to a proximal end of the cutter shaft.

7. The method of claim 1, further comprising a housing bearing disposed in the housing and having a through-hole for rotatably receiving the cutter shaft.

8. The method of claim 1, further comprising a first housing bearing disposed proximally of the gear of the cutter assembly and a second housing bearing disposed distally of the gear of the cutter assembly, a through-hole of the first and second housing bearings receiving the cutter shaft.

9. The method of claim 1, wherein the first driver is positioned between the motor and the second driver and is adapted to drive the second driver.

10. A method for removing bone comprising:
    providing a surgical tool having an oscillating cutter for cutting a bone, comprising:
    a housing having a handle;
    a motor mounted in the housing and having a rotatable output shaft;
    a cutter assembly having a cutter shaft carried by the housing, a cutter on a distal end of the cutter shaft and a gear disposed proximally of the cutter; and a transmission mounted in the housing and coupled to the motor output shaft, the transmission including:
   a first driver coupled to the output shaft and including:
      a crank coupled to the motor output shaft; and
      a circular crank bearing radially offset from a center of rotation of the crank;
   a second driver coupled to the first driver operationally downstream thereof, the second driver being coupled to the cutter shaft and being operable to effect linear reciprocation of the cutter shaft and transmit the rotary oscillation driving from the first driver to the cutter shaft, the second driver including a follower assembly having:
      a follower having a pair of arms defining a circular and cylindrical channel and a gear rack in mesh with the gear of the cutter shaft;
      a follower bearing disposed in the channel and receiving the crank bearing such that rotation of the crank bearing causes rotary oscillation of the follower;
wherein rotary oscillation of the follower causes oscillating rotation of the cutter shaft gear, and
removing the bone using the surgical tool.

11. The method of claim 10, further comprising a drive arm coupling the crank to the crank bearing.

12. The method of claim 11, wherein the crank bearing is a spherical bearing.

13. The method of claim 10, wherein the follower assembly includes an axle pivotally connected to the follower between the channel and the gear rack to allow oscillating motion of the follower.

14. The method of claim 13, further comprising a shaft bearing rotatably coupled to the axle and attached to a proximal end of the cutter shaft.

15. The method of claim 10, further comprising a housing bearing disposed in the housing and having a through-hole for rotatably receiving the cutter shaft.

16. The method of claim 10, further comprising a first housing bearing disposed proximally of the gear of the cutter assembly and a second housing bearing disposed distally of the gear of the cutter assembly, a through-hole of the first and second housing bearings receiving the cutter shaft.

17. The method of claim 10, wherein the first driver is positioned between the motor and the second driver and is adapted to drive the second driver.

18. The method of claim 10, wherein the gear rack is a curved sector gear.

19. The method of claim 18, wherein the sector gear has an inner edge curved in a circular arc with a radius approximately equal to its spacing from the center of rotation.

20. The method of claim 19, wherein the sector gear has an outer edge curved in an arc with a radius approximately equal to its spacing from the center of rotation.

* * * * *